United States Patent
Ma et al.

(10) Patent No.: US 9,873,713 B2
(45) Date of Patent: Jan. 23, 2018

(54) PROCESS FOR SYNTHESIZING HIGHLY OPTICALLY ACTIVE 1,3-DISUBSTITUTED ALLENES

(71) Applicant: Zhejiang University, Hangzhou, Zhejiang (CN)

(72) Inventors: Shengming Ma, Hangzhou (CN); Xin Huang, Hangzhou (CN); Chunling Fu, Hangzhou (CN)

(73) Assignee: ZHEJIANG UNIVERSITY, Hangzhou, Zhejiang (CN)

( * ) Notice: Subject to any disclaimer, the term of this patent is extended or adjusted under 35 U.S.C. 154(b) by 184 days.

(21) Appl. No.: 14/405,092

(22) PCT Filed: Oct. 10, 2014

(86) PCT No.: PCT/CN2014/088308
§ 371 (c)(1),
(2) Date: Dec. 2, 2014

(87) PCT Pub. No.: WO2016/019630
PCT Pub. Date: Feb. 11, 2016

(65) Prior Publication Data
US 2016/0185812 A1 Jun. 30, 2016

(30) Foreign Application Priority Data
Aug. 6, 2014 (CN) .......................... 2014 1 0384975

(51) Int. Cl.
| | | |
|---|---|---|
| *C07H 15/18* | (2006.01) |
| *C07H 15/10* | (2006.01) |
| *C07C 29/46* | (2006.01) |
| *C07C 2/86* | (2006.01) |
| *C07C 303/40* | (2006.01) |
| *C07C 231/12* | (2006.01) |
| *C07C 269/06* | (2006.01) |
| *C07C 67/30* | (2006.01) |
| *C07H 1/00* | (2006.01) |
| *C07C 37/14* | (2006.01) |
| *C07H 15/14* | (2006.01) |
| *C07C 29/32* | (2006.01) |
| *C07C 67/343* | (2006.01) |

(52) U.S. Cl.
CPC ............ *C07H 15/18* (2013.01); *C07C 2/867* (2013.01); *C07C 29/32* (2013.01); *C07C 29/46* (2013.01); *C07C 37/14* (2013.01); *C07C 67/30* (2013.01); *C07C 67/343* (2013.01); *C07C 231/12* (2013.01); *C07C 269/06* (2013.01); *C07C 303/40* (2013.01); *C07H 1/00* (2013.01); *C07H 15/10* (2013.01); *C07H 15/14* (2013.01); *C07B 2200/07* (2013.01); *C07C 2527/122* (2013.01); *C07C 2601/14* (2017.05)

(58) Field of Classification Search
CPC .......... C07H 15/18; C07H 1/00; C07H 15/10; C07C 29/46; C07C 37/14; C07C 303/40; C07C 231/12; C07C 269/06; C07C 67/30; C07C 2/867; C07C 2101/14; C07C 2527/122
USPC .... 536/17.2, 18.2, 18.4, 18.6; 560/157, 201; 564/187, 98; 568/743, 813, 828, 903; 585/438
See application file for complete search history.

(56) References Cited

PUBLICATIONS

Ye et al. Catalytic Asymmetric Synthesis of Optically Active Allenes from Terminal Alkynes. Org. Lett., vol. 14, No. 5, 1346-1349. 2012 and Supplementary Information, p. S1-S86.*
Li et al. Studies on Cu-catalyzed asymmetric alkynylation of tetrahydroisoquinoline derivatives. Tetrahedron: Asymmetry 17:590-597, 2006.*
Kuang et al. An Efficient Synthesis of Terminal Allenes from Terminal 1-Alkynes. J. Org. Chem 74, 1763-1765, 2009.*

* cited by examiner

*Primary Examiner* — Yih-Horng Shiao
(74) *Attorney, Agent, or Firm* — Birch, Stewart, Kolasch & Birch, LLP

(57) ABSTRACT

The present invention relates to a process for efficiently synthesizing highly optically active 1,3-disubstituted allenes, i.e., a one-step process for preparing highly optically active 1,3-disubstituted allenes by using a functionalized terminal alkyne, an aldehyde and a chiral α,α-diphenyl prolinol as reactants under the catalysis of a divalent copper salt. The operation of the process is simple, and the raw materials and reagents are readily available. The process has a broad-spectrum of substrates and a good compatibility for a wide variety of functional groups such as glycosidic units, primary alcohols, secondary alcohols, tertiary alcohols, amides, malonates, etc., and does not require the protection for the functional groups. The obtained axially chiral allene has a moderate to high yield and a good diastereoselectivity or enantioselectivity.

5 Claims, No Drawings

PROCESS FOR SYNTHESIZING HIGHLY OPTICALLY ACTIVE 1,3-DISUBSTITUTED ALLENES

TECHNICAL FIELD

The present invention relates to a chemical synthetic process, particularly to a process for synthesizing highly optically active 1,3-disubstituted allenes.

BACKGROUND

Due to the unique structure and active reactive performances of allene compounds as well as their more and more important role played in the organic syntheses, the allene chemistry has attracted more and more attentions (S. Yu, S. Ma, *Angew. Chem., Int. Ed.* 2012, 51, 3074; M. A. Tius, *Chem. Soc. Rev.* 2014, 43, 2979; J. L. Bras, J. Muzart, *Chem. Soc. Rev.* 2014, 43, 3003; S. Kitagaki, F. Inagaki, C. Mukai, *Chem. Soc. Rev.* 2014, 43, 2956; M. P. Muñoz, *Chem. Soc. Rev.* 2014, 43, 3164; C. S. Adams, C. D. Weatherly, E. G. Burke, J. M. Schomaker *Chem. Soc. Rev.* 2014, 43, 3136; R. Zimmer, H. U. Reissig, *Chem. Soc. Rev.,* 2014, 43, 2888; m) W. Yang, A. S. K. Hashmi, *Chem. Soc. Rev.,* 2014, 43, 2941; B. Alcaide, P. Almendros, C. Aragoncillo, *Chem. Soc. Rev.* 2014, 43, 3106; T. Cañeque, F. M. Truscott, R. Rodriguez, G. Maestri, M. Malacria, *Chem. Soc. Rev.* 2014, 43, 2916; F. López, J. L. Mascareñas, *Chem. Soc. Rev.* 2014, 43, 2904; Z. Wang, X. Xu, O. Kwon, *Chem. Soc. Rev.* 2014, 43, 2927). Therefore, how to simply and efficiently synthesize various allene compounds, especially 1,3-disubstituted allenes having an axial chirality activity, has become one of the issues of increasing concern to the chemists (L. K. Sydnes, *Chem. Rev.* 2003, 103, 1133; N. Krause, A. Hoffmann-Röder, *Tetrahedron* 2004, 60, 11671; K. M. Brummond, J. E. Deforrest, Synthesis 2007, 795; M. Ogasawara, *Tetrahedron: Asymmetry* 2009, 20, 259; g) S. Yu, S. Ma, *Chem. Commun.,* 2011, 47, 5384). The earlier synthetic methods of optically active 1,3-substituted allenes require the use of hazardous chemicals such as n-butyl lithium or ethyl magnesium bromide and lithium aluminum hydride, and the operations are inconvenient, which were unbeneficial to the large scale synthesis (L.-I. Olsson, A. Claesson, *Acta Chem. Scand.* 1977, B31, 614; A. Claesson, L.-I. Olsson, *J. Am. Chem. Soc.* 1979, 101, 7302; R. A. Smith, R. L. White, A. Krantz, *J. Med. Chem.* 1988, 31, 1558; J. Stichler-Bonaparte, H. Kruth, R. Lunkwitz, C. Tschierske, *Liebigs Ann.* 1996, 1375). Recently our team developed a series of processes for synthesizing optically active 1,3-disubstituted allenes by using terminal alkynes, aldehydes and chiral amines under the promotion of a zinc salt or under the co-promotion of a zinc salt and a monovalent copper salt. Although these processes have made great progress compared to the traditional methods, there are still some shortcomings such as a narrow substrate range, the requirement of large amount of metallic salts, going through a multi-step operation of the protection and deprotection for some specific functional groups (J. Ye, S. Li, B. Chen, W. Fan, J. Kuang, J. Liu, Y. Liu, B. Miao, B. Wan, Y. Wang, X. Xie, Q. Yu, W. Yuan, S. Ma, *Org. Lett.* 2012, 14, 1346; J. Ye, W. Fan, S. Ma, *Chem. Eur J.* 2013, 19, 716; J. Ye, R. Lu, W. Fan, S. Ma, *Tetrahedron* 2013, 69, 8959; R. Lü, J. Ye, T. Cao, B. Chen, W. Fan, W. Lin, J. Liu, H. Luo, B. Miao, S. Ni, X. Tang, N. Wang, Y. Wang, X. Xie, Q. Yu, W. Yuan, W. Zhang, C. Zhu, S. Ma, *Org. Lett.* 2013, 15, 2254).

The present invention overcomes all the drawbacks of the prior arts, which provides a one-step process for simply and efficiently preparing highly optically active 1,3-disubstituted allenes by using a divalent copper salt as the catalyst and using a terminal alkyne and chiral α,α-diphenyl prolinol as reactants.

SUMMARY OF THE INVENTION

The object of the present invention is to provide a simple and efficient process for synthesizing highly optically active 1,3-disubstituted allenes, i.e., a one-step process for preparing highly optically active 1,3-disubstituted allenes by using a functionalized terminal alkyne, an aldehyde and chiral α,α-diphenyl prolinol as reactants under the catalysis of a divalent copper salt.

The object of the present invention is achieved by using the following solution:

The present invention discloses a process for efficiently synthesizing highly optically active 1,3-disubstituted allenes, which uses a functionalized terminal alkyne, an aldehyde and a chiral secondary amine as reactants under the catalysis of a divalent copper salt and thereby produces a variety of functionalized axially chiral 1,3-disubstituted allenes by the heated reaction in an organic solvent. The reaction has a following reaction equation:

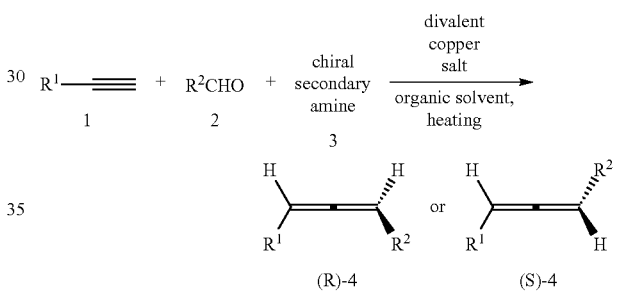

wherein $R^1$ comprises a variety of functional groups such as glycosidic units, primary alcohols, secondary alcohols, tertiary alcohols, amides, malonates, alkyl group or aryl group, and $R^2$ is an alkyl group or an aryl group.

As a further improvement, the present process comprises the following steps:

1) under nitrogen atmosphere, a divalent copper salt, a chiral secondary amine, a terminal alkyne, an aldehyde and an organic solvent were added in sequence into a reaction tube subjected to the anhydrous and anaerobic treatment, heating for reaction for 12-24 h;

2) after the completion of the reaction of step 1), raising the reaction tube from the oil bath, naturally returning to the room temperature, diluting with an organic solvent, transferring the liquid to a separatory funnel, washing with dilute hydrochloric acid, separating the organic phase, extracting the aqueous phase with the same organic solvent, combining the organic phases, washing with saturated brine, drying with anhydrous sodium sulfate, filtering, concentrating and subjecting to the column chromatography, so as to obtain the product axially chiral allene.

As a further improvement, the present process uses a divalent copper salt as catalyst, the catalyst is copper bromide, copper chloride, copper acetate, copper sulfate or copper triflate.

As a further improvement, the chiral secondary amine used in the present invention is (S)-3a or its enantiomers, and the structural variants (S)-3b and (S)-3c using (S)-3a as a template or their enantiomers.

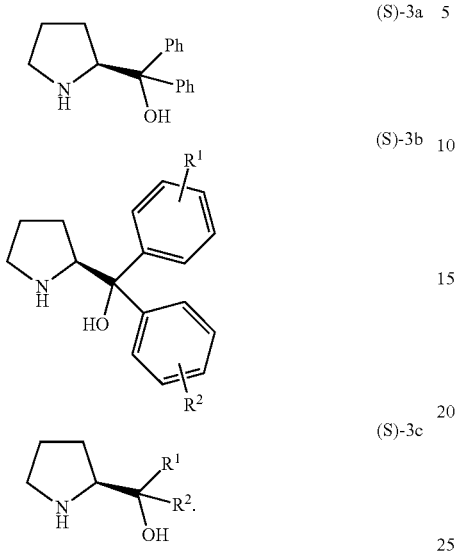

As a further improvement, the organic solvent used in the present invention is 1,4-dioxane, toluene, benzene, chlorobenzene, p-xylene, o-xylene, m-xylene, or mesitylene.

The present invention overcomes the drawbacks of the traditional methods, which has the following advantages: (1) greatly reduces the amount of metallic salt catalyst used; (2) has a broader spectrum of substrates and a good compatibility for functional groups, and does not require the protection for the functional groups; (3) the reaction has an excellent diastereoselectivity or enantioselectivity; and (4) the product is easy to separate and purify.

The innovation point of the present invention lies in developing a simple and efficient process for synthesizing highly optically active 1,3-disubstituted allenes, and for the first time discovering that a divalent copper salt can directly catalyzing the three-component reaction consisting of a terminal alkyne, an aldehyde and a chiral secondary amine, and that the reaction has a good selectivity wherein both de value and ee value are greater than 90%.

PREFERRED EMBODIMENTS OF THE INVENTION

The following examples are given for further illustrating the specific solutions of the present invention.

EXAMPLE 1

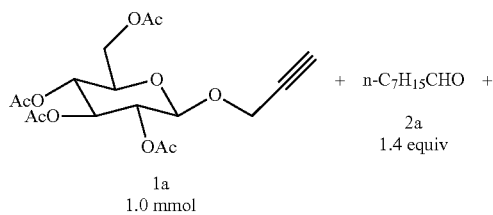

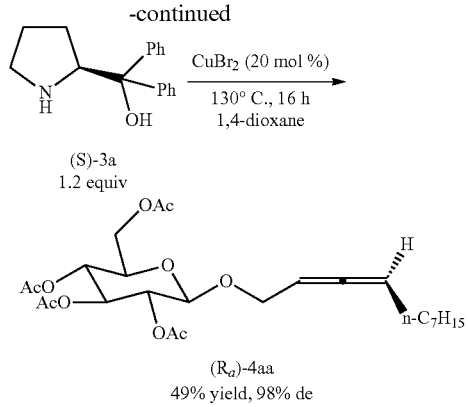

Wherein "equiv" refers to equivalent; "de" refers to diastereomeric excess; "ee" refers to enantiomeric excess.

To a flame-dried Schlenk tube were added $CuBr_2$ (44.9 mg, 0.2 mmol), 1a (387.0 mg, 1.0 mmol), (S)-3a (304.5 mg, 1.2 mmol), and 2a (180.1 mg, 1.4 mmol)/dioxane (3.0 mL) sequentially under nitrogen atmosphere. The Schlenk tube was then equipped with a condenser and the outlet connected to the vacuum line with a nitrogen flow was closed. The reaction was complete after being stirred at 130° C. for 16 h as monitored by TLC (eluent: petroleum ether/ethyl acetate=3/1). Then the resulting mixture was diluted with ethyl acetate (30 mL), and washed with an aqueous solution of hydrochloric acid (v/v=10%). The organic layer was separated, and the aqueous layer was extracted with ethyl acetate (20 mL). The combined organic layer was washed with brine and dried over anhydrous $Na_2SO_4$. After filtration and evaporation, the residue was purified by chromatography (eluent: petroleum ether/ethyl acetate=3/1) on silica gel to afford $(R_a)$-4aa (246.5 mg, 49%) as a liquid: 98% de (HPLC conditions: Chiralcel AS-H column, hexane/i-PrOH=95/5, 0.3 mL/min, $\lambda$=214 nm, $t_R$(major)=24.9 min, $t_R$(minor)=26.8 min); $[\alpha]_D^{20}$=−32.2 (c=1.07, $CHCl_3$); $^1$H NMR (300 MHz, $CDCl_3$) δ 5.28-4.95 (m, 5 H), 4.64 (d, J=7.8 Hz, 1 H), 4.35-4.24 (m, 2 H), 4.18-4.07 (m, 2 H), 3.74-3.63 (m, 1 H), 2.09 (s, 3 H, Me), 2.05 (s, 3 H, Me), 2.03 (s, 3 H, Me), 2.01 (s, 3 H, Me), 2.12-1.94 (m, 2 H, $CH_2$), 1.48-1.20 (m, 10 H, $CH_2\times5$), 0.89 (t, J=6.9 Hz, 3 H, Me); $^{13}$C NMR (75 Hz, $CDCl_3$) δ 205.4, 170.5, 170.2, 169.3, 169.2, 98.8, 92.1, 87.2, 72.8, 71.6, 71.0, 68.2, 67.8, 61.7, 31.7, 28.98, 28.95, 28.9, 28.3, 22.5, 20.6, 20.52, 20.45, 20.4, 13.9; IR (neat) ν ($cm^{-1}$) 2928, 2856, 1963, 1757, 1435, 1370, 1226, 1165, 1041; MS (ESI, m/z) 521 (M+$Na^+$), 516 (M+$NH_4^+$); Anal. Calcd. for $C_{25}H_{38}O_{10}$ (%): C, 60.23; H, 7.68; Found: C, 60.21; H, 7.37.

EXAMPLE 2

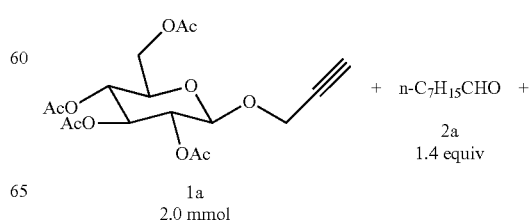

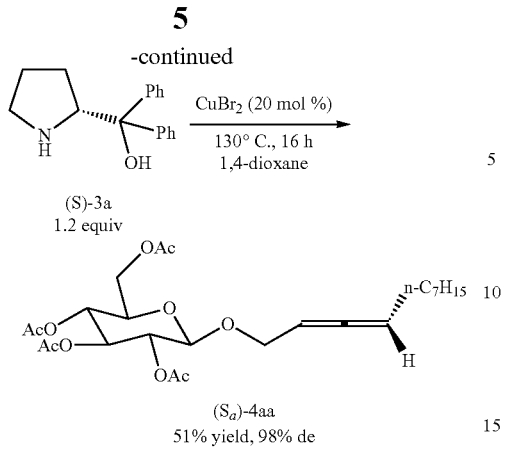

(S)-3a
1.2 equiv (S$_a$)-4aa
51% yield, 98% de

Following the procedure of Example 1. The reaction of CuBr$_2$ (89.3 mg, 0.4 mmol), 1a (772.5 mg, 2.0 mmol), (R)-3a (607.6 mg, 2.4 mmol), and 2a (360.6 mg, 2.8 mmol) in dioxane (6.0 mL) afforded (S$_a$)-4aa (508.2 mg, 51%) (eluent: petroleum ether/ethyl acetate=3/1) as a liquid: 98% de (HPLC conditions: Chiralcel AS-H column, hexane/i-PrOH=95/5, 0.4 mL/min, λ=214 nm, t$_R$(minor)=35.5 min, t$_R$(major)=36.5 min); $[\alpha]_D^{20}$=+36.8 (c=0.975, CHCl$_3$); $^1$H NMR (300 MHz, CDCl$_3$) δ 5.28-4.95 (m, 5 H), 4.64 (d, J=7.8 Hz, 1 H), 4.34-4.25 (m, 2 H), 4.18-4.07 (m, 2 H), 3.75-3.66 (m, 1 H), 2.08 (s, 3 H, Me), 2.04 (s, 3 H, Me), 2.03 (s, 3 H, Me), 2.00 (s, 3 H, Me), 2.12-1.95 (m, 2 H, CH$_2$), 1.48-1.18 (m, 10 H, CH$_2$×5), 0.88 (t, J=6.6 Hz, 3 H, Me); $^{13}$C NMR (75 Hz, CDCl$_3$) δ 205.1, 170.3, 169.9, 169.1, 169.0, 98.7, 92.0, 87.1, 72.6, 71.5, 70.9, 68.1, 67.5, 61.6, 31.5, 28.8, 28.7, 28.1, 22.3, 20.39, 20.35, 20.3, 13.8; IR (neat) ν (cm$^{-1}$) 2929, 2857, 1962, 1759, 1435, 1367, 1227, 1166, 1040; MS (ESI, m/z) 516 (M+NH$_4^+$); Anal. Calcd. for C$_{25}$H$_{38}$O$_{10}$ (%): C, 60.23; H, 7.68; Found: C, 60.61; H, 7.71.

EXAMPLE 3

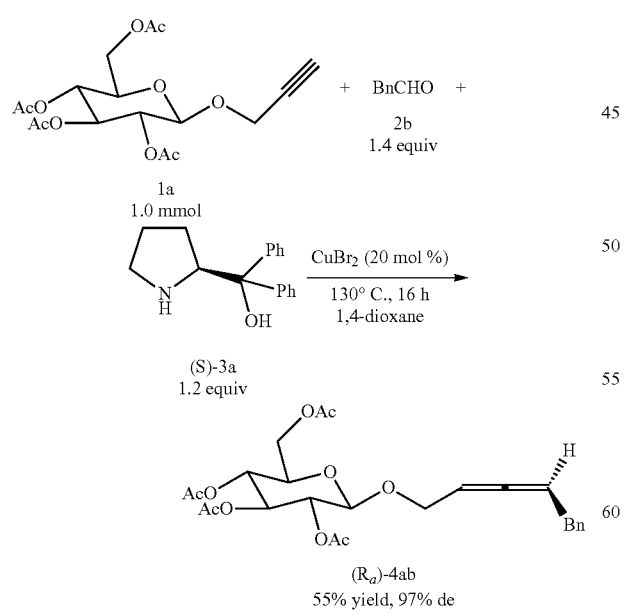

(R$_a$)-4ab
55% yield, 97% de

Following the procedure of Example 1. The reaction of CuBr$_2$ (44.9 mg, 0.2 mmol), 1a (388.1 mg, 1.0 mmol), (S)-3a (303.3 mg, 1.2 mmol), and 2b (168.8 mg, 1.4 mmol) in dioxane (3.0 mL) afforded (R$_a$)-4ab (273.0 mg, 55%) (eluent: petroleum ether/ethyl acetate=2.5/1) as a liquid: 97% de (HPLC conditions: Chiralcel IA-H column, hexane/i-PrOH=95/5, 1.0 mL/min, λ=214 nm, t$_R$(major)=16.4 min, t$_R$(minor)=23.0 min); $[\alpha]_D^{20}$=−30.4 (c=1.405, CHCl$_3$); $^1$H NMR (300 MHz, CDCl$_3$) δ 7.39-7.19 (m, 5 H, ArH), 5.50-5.37 (m, 1 H), 5.22-5.11 (m, 2 H), 5.06 (t, J=9.6 Hz, 1 H), 4.95 (t, J=8.9 Hz, 1 H), 4.35 (d, J=7.8 Hz, 1 H), 4.32-4.19 (m, 2 H), 4.13-4.02 (m, 2 H), 3.55-3.29 (m, 3 H), 2.07 (s, 3 H, Me), 2.029 (s, 3 H, Me), 2.026 (s, 3 H, Me), 2.00 (s, 3 H, Me); $^{13}$C NMR (75 Hz, CDCl$_3$) δ 205.7, 170.4, 170.0, 169.15, 169.06, 139.2, 128.34, 128.28, 126.3, 98.2, 91.5, 88.0, 72.5, 71.3, 70.8, 68.0, 67.0, 61.5, 34.7, 20.5, 20.42, 20.35; IR (neat) ν (cm$^{-1}$) 3063, 3028, 2945, 2884, 1964, 1756, 1602, 1495, 1450, 1433, 1370, 1226, 1165, 1041; MS (ESI, m/z) 529 (M+K$^+$), 513 (M+Na$^+$), 508 (M+NH$_4^+$); Anal. Calcd. for C$_{25}$H$_{30}$O$_{10}$ (%): C, 61.22; H, 6.16; Found: C, 61.32; H, 6.03.

EXAMPLE 4

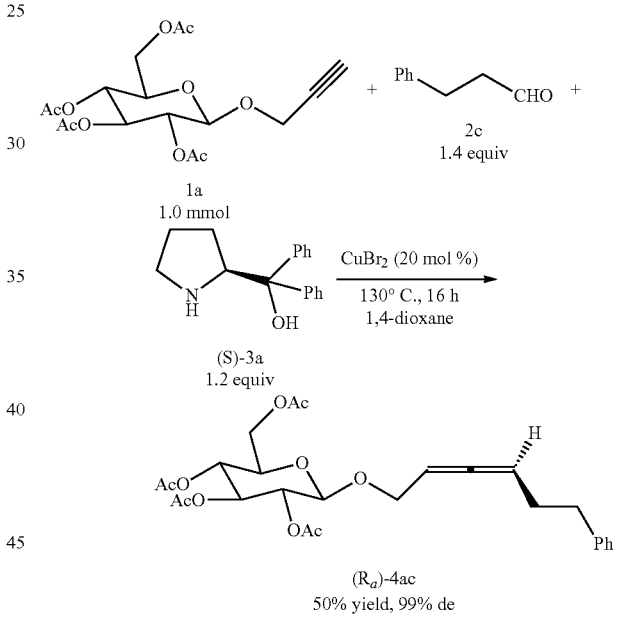

(R$_a$)-4ac
50% yield, 99% de

Following the procedure of Example 1. The reaction of CuBr$_2$ (44.7 mg, 0.2 mmol), 1a (386.1 mg, 1.0 mmol), (S)-3a (303.5 mg, 1.2 mmol), and 2c (187.6 mg, 1.4 mmol) in dioxane (3.0 mL) afforded (R$_a$)-4ac (253.4 mg, 50%) (eluent: petroleum ether/ethyl acetate=2.5/1) as a liquid: 99% de (HPLC conditions: Chiralcel OD-H column, hexane/i-PrOH=90/10, 1.0 mL/min, λ=214 nm, t$_R$(major)=13.1 min, t$_R$(minor)=19.3 min); $[\alpha]_D^{20}$=−37.7 (c=1.32, CHCl$_3$); $^1$H NMR (300 MHz, CDCl$_3$) δ 7.34-7.15 (m, 5 H), 5.31-4.95 (m, 5 H, ArH), 4.57 (d, J=8.1 Hz, 1 H), 4.32-4.18 (m, 2 H), 4.16-4.01 (m, 2 H), 3.70-3.61 (m, 1 H), 2.74 (t, J=7.7 Hz, 2 H), 2.40-2.28 (m, 2 H), 2.07 (s, 3 H, Me), 2.03 (s, 3 H, Me), 2.02 (s, 3 H, Me), 2.00 (s, 3 H, Me); $^{13}$C NMR (75 Hz, CDCl$_3$) δ 205.3, 170.5, 170.2, 169.3, 169.2, 141.2, 128.4, 128.2, 125.9, 99.2, 91.5, 87.9, 72.8, 71.7, 71.2, 68.3, 67.7, 61.8, 35.1, 30.0, 20.59, 20.56, 20.49, 20.47; IR (neat) ν (cm$^{-1}$) 3063, 3024, 2942, 2861, 1964, 1757, 1603, 1496, 1453, 1432, 1369, 1225, 1165, 1041; MS (ESI, m/z)

527 (M+Na$^+$), 522 (M+NH$_4^+$); Anal. Calcd. for C$_{26}$H$_{32}$O$_{10}$ (%): C, 61.90; H, 6.39; Found: C, 61.41; H, 6.25. HRMS calcd. for C$_{26}$H$_{36}$NO$_{10}$ (M+NH$_4^+$): 522.2334; Found: 522.2322.

EXAMPLE 5

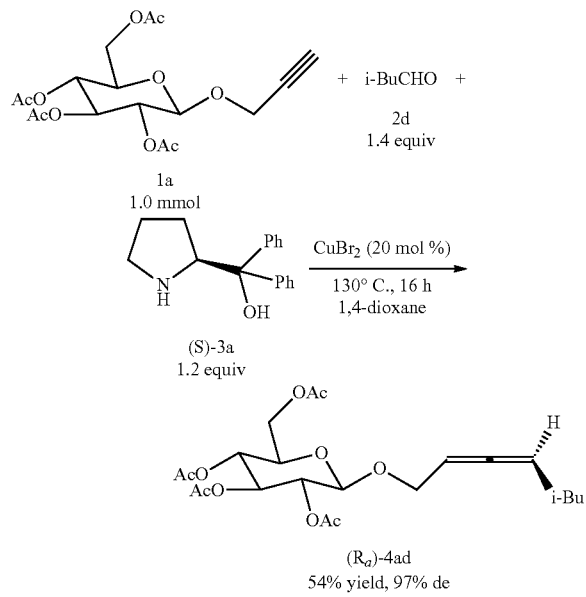

1a
1.0 mmol (S)-3a
1.2 equiv (R$_a$)-4ad
54% yield, 97% de

Following the procedure of Example 1. The reaction of CuBr$_2$ (45.0 mg, 0.2 mmol), 1a (385.4 mg, 1.0 mmol), (S)-3a (304.1 mg, 1.2 mmol), and 2d (121.2 mg, 1.4 mmol) in dioxane (3.0 mL) afforded (R$_a$)-4ad (245.2 mg, 54%) (eluent: petroleum ether/ethyl acetate=3/1) as a solid: 97% de (HPLC conditions: Chiralcel AD-H column, hexane/i-PrOH=95/5, 1.0 mL/min, λ=214 nm, $t_R$(minor)=17.6 min, $t_R$(major)=18.9 min); $[α]_D^{20}$=−26.7 (c=1.00, CHCl$_3$); m.p. 68-69° C. (DCM/n-hexane); $^1$H NMR (300 MHz, CDCl$_3$) δ 5.28-4.95 (m, 5 H), 4.63 (d, J=8.1 Hz, 1 H), 4.36-4.21 (m, 2 H), 4.20-4.04 (m, 2 H), 3.73-3.61 (m, 1 H), 2.09 (s, 3 H, Me), 2.06 (s, 3 H, Me), 2.04 (s, 3 H, Me), 2.02 (s, 3 H, Me), 2.17-1.87 (m, 2 H, CH$_2$), 1.76-1.59 (m, 1 H, CH), 0.94 (d, J=6.6 Hz, 6 H, Me×2); $^{13}$C NMR (75 Hz, CDCl$_3$) δ 205.9, 170.5, 170.2, 169.23, 169.16, 98.8, 90.5, 86.5, 72.7, 71.6, 71.0, 68.1, 67.8, 61.7, 37.8, 28.1, 22.0, 21.9, 20.54, 20.51, 20.44, 20.42; IR (KBr) ν (cm$^{-1}$) 2957, 2871, 1964, 1757, 1434, 1369, 1226, 1165, 1041; MS (ESI, m/z) 479 (M+Na$^+$), 474 (M+NH$_4^+$); Anal. Calcd. for C$_{22}$H$_{32}$O$_{10}$ (%): C, 57.88; H, 7.07; Found: C, 57.89; H, 7.08.

EXAMPLE 6

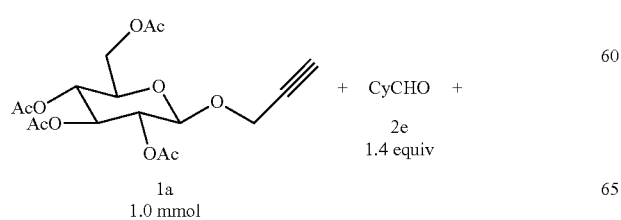

1a
1.0 mmol

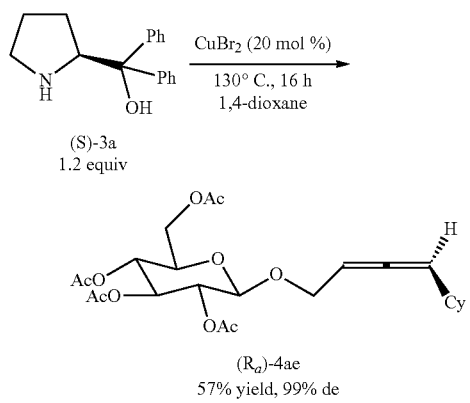

(S)-3a
1.2 equiv (R$_a$)-4ae
57% yield, 99% de

Following the procedure of Example 1. The reaction of CuBr$_2$ (45.0 mg, 0.2 mmol), 1a (388.5 mg, 1.0 mmol), (S)-3a (305.5 mg, 1.2 mmol), and 2e (157.5 mg, 1.4 mmol) in dioxane (3.0 mL) afforded (R$_a$)-4ae (275.1 mg, 57%) (eluent: petroleum ether/ethyl acetate=3/1) as a solid: 99% de (HPLC conditions: Chiralcel AD-H column, hexane/i-PrOH=95/5, 1.0 mL/min, λ=214 nm, $t_R$(minor)=16.4 min, $t_R$(major)=19.1 min); $[α]_D^{20}$=(c=0.92, CHCl$_3$); m.p. 102-103° C. (DCM/n-hexane); $^1$H NMR (300 MHz, CDCl$_3$) δ 5.27-4.96 (m, 5 H), 4.66 (d, J=8.1 Hz, 1 H), 4.36-4.22 (m, 2 H), 4.19-4.05 (m, 2 H), 3.72-3.63 (m, 1 H), 2.09 (s, 3 H, Me), 2.05 (s, 3 H, Me), 2.03 (s, 3 H, Me), 2.01 (s, 3 H, Me), 2.22-1.89 (m, 1 H, CH), 1.81-1.60 (m, 5 H, CH$_2$×2 and one proton of CH$_2$), 1.40-1.00 (m, 5 H, CH$_2$×2 and one proton of CH$_2$); $^{13}$C NMR (75 Hz, CDCl$_3$) δ 204.3, 170.4, 170.0, 169.2, 169.1, 98.7, 98.0, 88.1, 72.7, 71.5, 71.0, 68.1, 67.8, 61.6, 36.6, 32.8, 32.6, 25.8, 25.6, 20.5, 20.42, 20.36; IR (KBr) ν (cm$^{-1}$) 2925, 2851, 1965, 1741, 1447, 1412, 1380, 1287, 1260, 1227, 1171, 1115, 1094, 1058, 1036; MS (ESI, m/z) 505 (M+Na$^+$), 500 (M+NH$_4^+$); Anal. Calcd. for C$_{24}$H$_{34}$O$_{10}$ (%): C, 59.74; H, 7.10; Found: C, 59.80; H, 7.04.

EXAMPLE 7

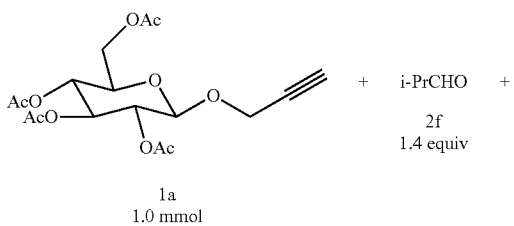

1a
1.0 mmol

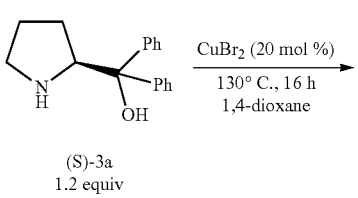

(S)-3a
1.2 equiv

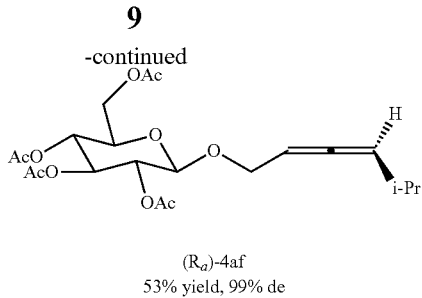

(R$_a$)-4af
53% yield, 99% de

Following the procedure of Example 1. The reaction of CuBr$_2$ (44.7 mg, 0.2 mmol), 1a (384.2 mg, 1.0 mmol), (S)-3a (305.5 mg, 1.2 mmol), and 2f (101.4 mg, 1.4 mmol) in dioxane (3.0 mL) afforded (R$_a$)-4af (233.9 mg, 53%) (eluent: petroleum ether/ethyl acetate=2.5/1) as a liquid: 99% de (HPLC conditions: Chiralcel IA-H column, hexane/i-PrOH=95/5, 1.0 mL/min, λ=214 nm, t$_R$(minor)=15.1 min, t$_R$(major)=16.1 min); [α]$_D^{20}$=−23.1 (c=1.08, CHCl$_3$); $^1$H NMR (300 MHz, CDCl$_3$) δ 5.30-5.14 (m, 3 H), 5.10 (t, J=9.6 Hz, 1 H), 5.01 (dd, J$_1$=9.6 Hz, J$_2$=8.1 Hz, 1 H), 4.66 (d, J=7.8 Hz, 1 H), 4.36-4.24 (m, 2 H), 4.17-4.07 (m, 2 H), 3.72-3.64 (m, 1 H), 2.40-2.24 (m, 1 H, CH), 2.09 (s, 3 H, Me), 2.05 (s, 3 H, Me), 2.03 (s, 3 H, Me), 2.01 (s, 3 H, Me), 1.03 (d, J=6.6 Hz, 6 H, Me×2); $^{13}$C NMR (75 Hz, CDCl$_3$) δ 204.0, 170.5, 170.2, 169.3, 169.2, 99.5, 98.7, 88.5, 72.8, 71.6, 71.1, 68.2, 67.9, 61.8, 27.5, 22.3, 22.2, 20.6, 20.51, 20.45, 20.4; IR (neat) ν (cm$^{-1}$) 2962, 2871, 1961, 1755, 1434, 1367, 1227, 1165, 1040; MS (ESI, m/z) 460 (M+NH$_4^+$); Anal. Calcd. for C$_{21}$H$_{30}$O$_{10}$ (%): C, 57.01; H, 6.83; Found: C, 57.05; H, 6.72.

EXAMPLE 8

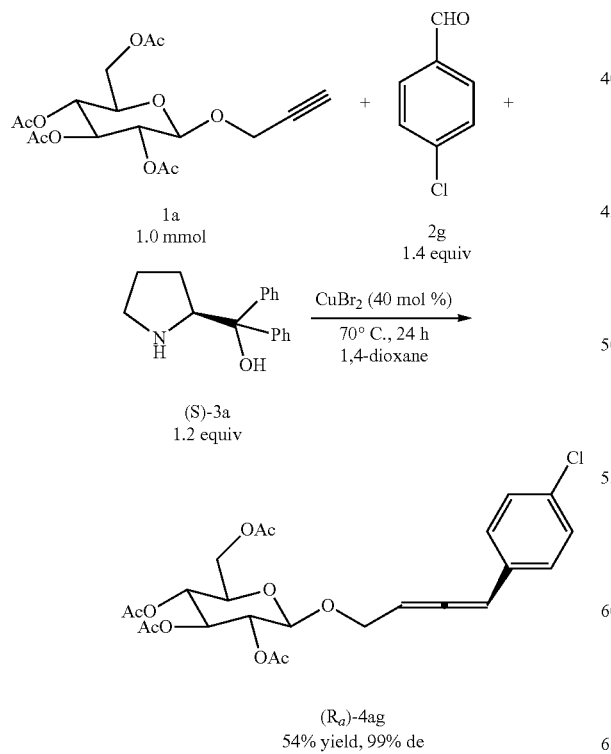

(R$_a$)-4ag
54% yield, 99% de

Following the procedure of Example 1. The reaction of CuBr$_2$ (89.7 mg, 0.4 mmol), 1a (386.8 mg, 1.0 mmol), (S)-3a (304.6 mg, 1.2 mmol), and 2g (196.8 mg, 1.4 mmol) in dioxane (3.0 mL) afforded (R$_a$)-4ag (277.3 mg, 54%) (eluent: petroleum ether/ethyl acetate=2/1) as a liquid: 99% de (HPLC conditions: Chiralcel AD-H column, hexane/i-PrOH=95/5, 0.6 mL/min, λ=214 nm, t$_R$(major)=57.1 min, t$_R$(minor)=62.3 min); [α]$_D^{20}$=−111.8 (c=1.04, CHCl$_3$); $^1$H NMR (300 MHz, CDCl$_3$) δ 7.34-7.27 (m, 2 H, ArH), 7.25-7.19 (m, 2 H, ArH), 6.23 (dt, J$_1$=6.2 Hz, J$_2$=2.3 Hz, 1 H, one proton of CH=C=CH), 5.65 (dd, J$_1$=13.8 Hz, J$_2$=6.3 Hz, 1 H, one proton of CH=C=CH), 5.22 (t, J=9.5 Hz, 1 H), 5.14-4.97 (m, 2 H), 4.65 (d, J=7.8 Hz, 1 H), 4.47-4.37 (m, 1 H), 4.29-4.18 (m, 2 H), 4.10 (dd, J$_1$=12.3 Hz, J$_2$=2.4 Hz, 1 H), 3.66-3.58 (m, 1 H), 2.03 (s, 3 H, Me), 2.02 (s, 3 H, Me), 2.00 (s, 3 H, Me), 1.99 (s, 3 H, Me); $^{13}$C NMR (75 Hz, CDCl$_3$) δ 206.4, 170.3, 169.9, 169.1, 169.0, 132.8, 132.0, 128.7, 127.9, 99.2, 94.9, 91.8, 72.7, 71.7, 71.1, 68.2, 66.6, 61.7, 20.4, 20.3; IR (neat) ν (cm$^{-1}$) 2956, 2925, 2869, 2849, 1953, 1755, 1492, 1456, 1429, 1376, 1224, 1039; MS (ESI, m/z) 535 (M($^{37}$Cl)+Na$^+$), 533 (M($^{35}$Cl)+Na$^+$), 530 (M($^{37}$Cl)+NH$_4^+$), 528 (M($^{35}$Cl)+NH$_4^+$); HRMS calcd. for C$_{24}$H$_{31}^{35}$ClNO$_{10}$ (M($^{35}$Cl)+NH$_4^+$): 528.1631; Found: 528.1614.

EXAMPLE 9

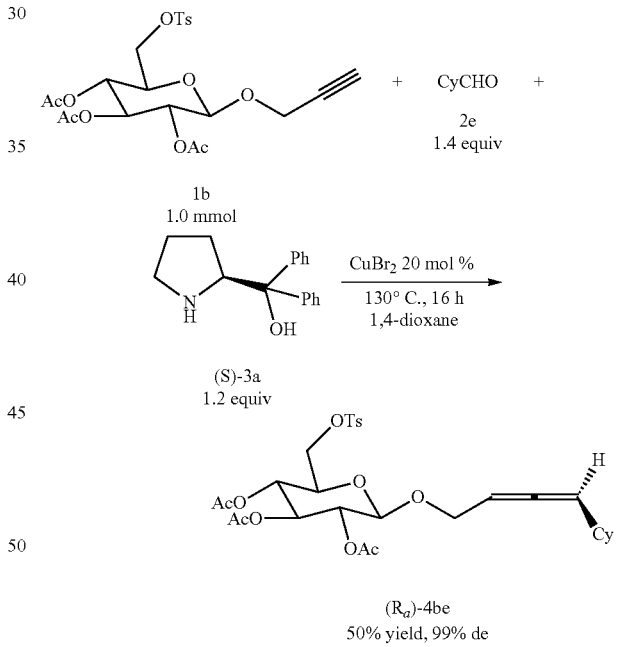

(R$_a$)-4be
50% yield, 99% de

Following the procedure of Example 1. The reaction of CuBr$_2$ (45.0 mg, 0.2 mmol), 1b (498.9 mg, 1.0 mmol), (S)-3a (304.1 mg, 1.2 mmol), and 2e (156.9 mg, 1.4 mmol) in dioxane (3.0 mL) afforded (R)-4be (297.4 mg, 50%) (eluent: petroleum ether/ethyl acetate=2.5/1) as a solid: 99% de (HPLC conditions: Chiralcel IA-H column, hexane/i-PrOH=80/20, 1.0 mL/min, λ=214 nm, t$_R$(minor)=9.5 min, t$_R$(major)=10.9 min); [α]$_D^{20}$=−21.6 (c=0.97, CHCl$_3$); m.p. 117-118° C. (EtOAc/n-hexane); $^1$H NMR (300 MHz, CDCl$_3$) δ 7.78 (d, J=8.4 Hz, 2 H, ArH), 7.35 (d, J=8.1 Hz, 2 H, ArH), 5.27-5.08 (m, 3 H), 4.97-4.86 (m, 2 H), 4.58 (d, J=8.1 Hz, 1 H), 4.27-4.17 (m, 1 H), 4.16-3.97 (m, 3 H), 3.77-3.68 (m, 1 H), 2.45 (s, 3 H), 2.03 (s, 3 H, Me), 2.00 (s, 3 H, Me), 1.99 (s, 3 H, Me), 2.10-1.95 (m, 1 H, CH), 1.82-1.59 (m, 5 H, CH$_2$×2 and one proton of CH$_2$), 1.40-0.98 (m, 5 H, CH$_2$×2 and one proton of CH$_2$); $^{13}$C NMR (75 Hz, CDCl$_3$) δ 204.2, 170.1, 169.3, 169.1, 145.0, 132.2, 129.8, 127.9, 98.7, 98.2, 88.2, 72.4, 71.3, 70.8, 68.4, 67.9, 67.5, 36.6, 32.8, 32.7, 25.9, 25.7, 21.5, 20.47, 20.42, 20.39; IR (KBr) ν (cm$^{-1}$) 2926, 2852, 1962, 1758, 1598, 1449, 1369, 1245, 1218, 1178, 1040; MS (ESI, m/z) 612 (M+NH$_4^+$); Anal. Calcd. for C$_{29}$H$_{38}$O$_{11}$S (%): C, 58.57; H, 6.44; Found: C, 58.81; H, 6.38.

EXAMPLE 10

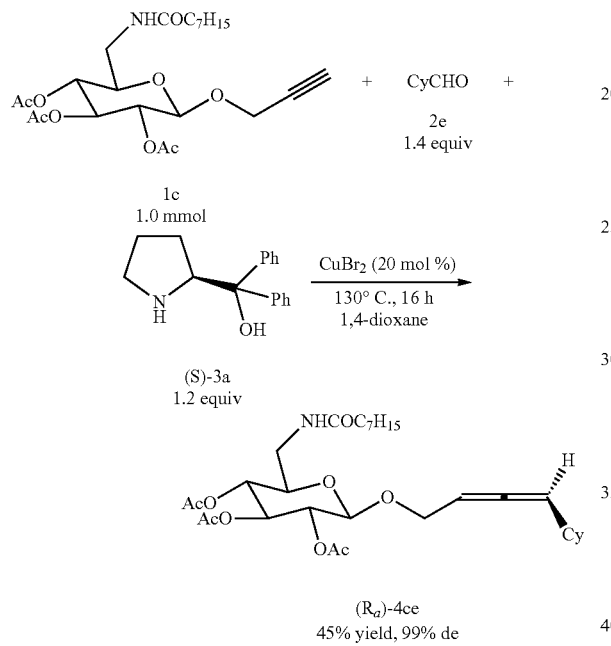

(R$_a$)-4ce
45% yield, 99% de

Following the procedure of Example 1. The reaction of CuBr$_2$ (44.9 mg, 0.2 mmol), 1c (472.5 mg, 1.0 mmol), (S)-3a (303.2 mg, 1.2 mmol), and 2e (158.1 mg, 1.4 mmol) in dioxane (3.0 mL) afforded (R$_a$)-4ce (256.2 mg, 45%) (eluent: petroleum ether/ethyl acetate=1.5/1) as a liquid: 99% de (HPLC conditions: Chiralcel AD-H column, hexane/i-PrOH=95/5, 1.0 mL/min, λ=214 nm, t$_R$(minor)=27.3 min, t$_R$(major)=29.6 min); [α]$_D^{20}$=-38.9 (c=1.35, CHCl$_3$); $^1$H NMR (300 MHz, CDCl$_3$) δ 5.89 (t, J=5.4 Hz, 1 H), 5.27-5.13 (m, 3 H), 5.02-4.85 (m, 2 H), 4.62 (d, J=8.1 Hz, 1 H), 4.34-4.24 (m, 1 H), 4.18-4.07 (m, 1 H), 3.61-3.40 (m, 3 H), 2.23-2.11 (m, 2 H), 2.06 (s, 3 H, Me), 2.05 (s, 3 H, Me), 2.00 (s, 3 H, Me), 2.10-1.95 (m, 1 H, CH), 1.82-1.54 (in, 7 H, CH$_2$×3 and one proton of CH$_2$), 1.39-1.00 (in, 1 3H, CH$_2$×6 and one proton of CH$_2$), 0.88 (t, J=6.6 Hz, 3 H, Me); $^{13}$C NMR (75 Hz, CDCl$_3$) δ 204.3, 173.1, 170.1, 169.5, 169.2, 99.2, 98.3, 88.3, 72.7, 72.4, 71.1, 68.7, 68.4, 38.8, 36.7, 36.5, 32.9, 32.7, 31.5, 29.1, 28.9, 25.9, 25.7, 25.4, 22.5, 20.52, 20.47, 13.9; IR (neat) ν (cm$^{-1}$) 3312, 2926, 2853, 1961, 1760, 1651, 1538, 1447, 1373, 1248, 1220, 1165, 1050; MS (ESI, m/z) 604 (M+K$^+$), 588 (M+Na$^+$), 566 (M+H$^+$); Anal. Calcd. for C$_{30}$H$_{47}$NO$_9$ (%): C, 63.70; H, 8.37; N, 2.48; Found: C, 63.60; H, 8.39; N, 2.29.

EXAMPLE 11

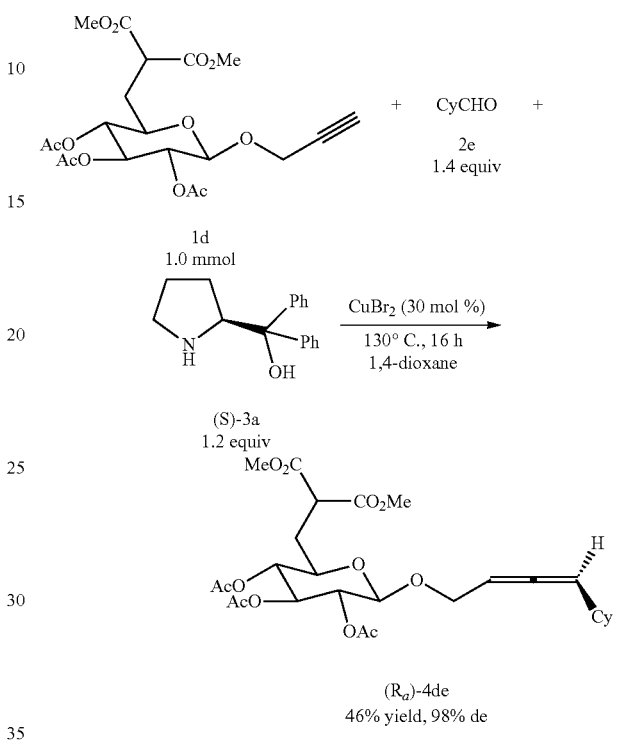

(R$_a$)-4de
46% yield, 98% de

Following the procedure of Example 1. The reaction of CuBr$_2$ (67.0 mg, 0.3 mmol), 1d (457.3 mg, 1.0 mmol), (S)-3a (304.0 mg, 1.2 mmol), and 2e (157.3 mg, 1.4 mmol) in dioxane (3.0 mL) afforded (R$_a$)-4de (255.0 mg, 46%) (eluent: petroleum ether/ethyl acetate=2.5/1) as a liquid: 98% de (HPLC conditions: Chiralcel AD-H column, hexane/i-PrOH=80/20, 0.5 mL/min, λ=214 nm, t$_R$(minor)=12.2 min, t$_R$(major)=14.3 min); [α]$_D^{20}$=-30.0 (c=1.375, CHCl$_3$); $^1$H NMR (300 MHz, CDCl$_3$) δ 5.26-5.12 (m, 3 H), 4.96 (dd, J$_1$=9.8 Hz, J$_2$=8.0 Hz, 1 H), 4.88 (t, J=9.5 Hz, 1 H), 4.52 (d, J=8.1 Hz, 1 H), 4.25 (ddd, J$_1$=11.4 Hz, J$_2$=6.3 Hz, J$_3$=2.7 Hz, 1 H), 4.06 (ddd, J$_1$=11.7 Hz, =7.5 Hz, J$_3$=2.4 Hz, 1 H), 3.76 (s, 3 H, Me), 3.74 (s, 3 H, Me), 3.67 (dd, J$_1$=9.6 Hz, J$_2$=5.1 Hz, 1 H), 3.52 (td, J$_1$=9.6 Hz, J$_1$=2.9 Hz, 1 H, CH), 2.30-2.19 (m, 1 H), 2.13-1.94 (m, 11 H), 1.81-1.60 (m, 5 H, CH$_2$×2 and one proton of CH$_2$), 1.40-1.00 (m, 5 H, CH$_2$×2 and one proton of CH$_2$); $^{13}$C NMR (75 Hz, CDCl$_3$) δ 204.1, 170.1, 169.5, 169.2, 169.1, 169.0, 99.2, 98.1, 88.3, 72.6, 71.6, 71.1, 71.0, 68.1, 52.6, 52.5, 47.4, 36.6, 32.8, 32.7, 30.2, 25.9, 25.7, 20.52, 20.49, 20.4; IR (neat) ν (cm$^{-1}$) 2927, 2852, 1961, 1755, 1436, 1367, 1245, 1218, 1159, 1046; MS (ESI, m/z) 577 (M+Na$^+$), 572 (M+NH$_4^+$); Anal. Calcd. for C$_{27}$H$_{38}$O$_{12}$ (%): C, 58.47; H, 6.91; Found: C, 58.04; H, 6.68. HRMS calcd. for C$_{27}$H$_{42}$N O$_{12}$ (M+NH$_4^+$): 572.2702; Found: 572.2688.

EXAMPLE 12

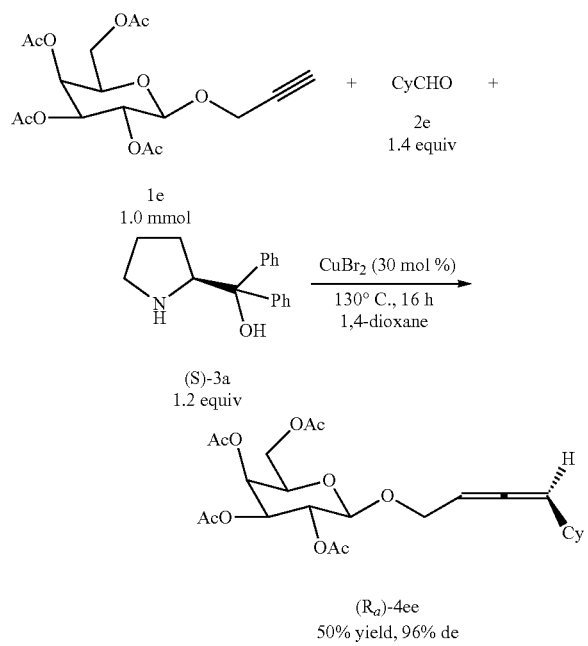

(R$_a$)-4ee
50% yield, 96% de

Following the procedure of Example 1. The reaction of CuBr$_2$ (67.3 mg, 0.3 mmol), 1e (388.0 mg, 1.0 mmol), (S)-3a (303.7 mg, 1.2 mmol), and 2e (158.0 mg, 1.4 mmol) in dioxane (3.0 mL) afforded (R$_a$)-4ee (240.3 mg, 50%) (eluent: petroleum ether/ethyl acetate=3/1) as a liquid: 96% de (HPLC conditions: Chiralcel AD-H column, hexane/i-PrOH=95/5, 1.0 mL/min, λ=214 nm, t$_R$(major)=20.0 min, t$_R$(minor)=23.5 min); [α]$_D^{20}$=−26.7 (c=1.24, CHCl$_3$); $^1$H NMR (300 MHz, CDCl$_3$) δ 5.40 (d, J=3.0 Hz, 1 H), 5.27-5.13 (m, 3 H), 5.02 (dd, J$_1$=10.4 Hz, J$_2$=3.2 Hz, 1 H), 4.62 (d, J=8.1 Hz, 1 H), 4.37-4.27 (m, 1 H), 4.23-4.07 (m, 3 H), 3.89 (t, J=6.6 Hz, 1 H), 2.16 (s, 3 H, Me), 2.09 (s, 3 H, Me), 2.06 (s, 3 H, Me), 1.99 (s, 3 H, Me), 2.20-1.93 (m, 1 H, CH), 1.83-1.60 (m, 5 H, CH$_2$×2 and one proton of CH$_2$), 1.40-0.99 (m, 5 H, CH$_2$×2 and one proton of CH$_2$); $^{13}$C NMR (75 Hz, CDCl$_3$) δ 204.3, 170.12, 170.09, 170.0, 169.2, 99.2, 98.0, 88.2, 70.8, 70.4, 68.6, 67.8, 66.8, 61.1, 36.6, 32.8, 32.6, 25.8, 25.7, 20.5, 20.43, 20.36; IR (neat) ν (cm$^{-1}$) 2926, 2852, 1961, 1754, 1449, 1370, 1223, 1170, 1132, 1075, 1057; MS (ESI, m/z) 505 (M+Na$^+$), 500 (M+NH$_4^+$); Anal. Calcd. for C$_{24}$H$_{34}$O$_{10}$ (%): C, 59.74; H, 7.10; Found: C, 59.77; H, 6.97.

EXAMPLE 13

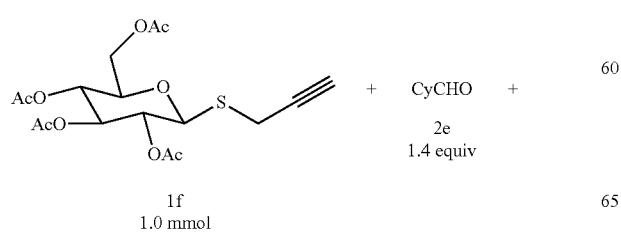

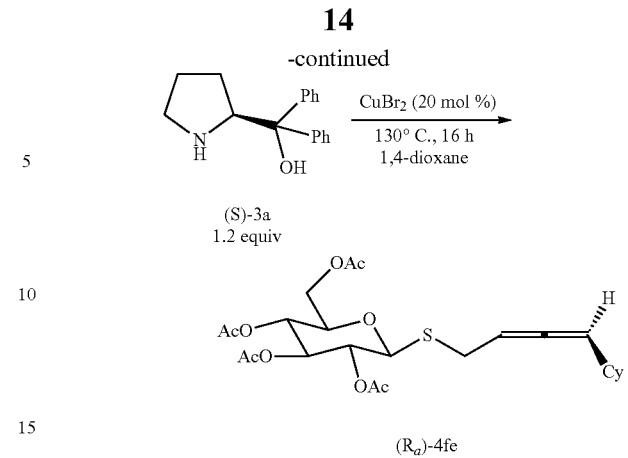

(R$_a$)-4fe
46% yield, 96% de

Following the procedure of Example 1. The reaction of CuBr$_2$ (44.9 mg, 0.2 mmol), 1f (400.8 mg, 1.0 mmol), (S)-3a (304.6 mg, 1.2 mmol), and 2e (157.2 mg, 1.4 mmol) in dioxane (3.0 mL) afforded (R$_a$)-4fe (230.3 mg, 46%) (eluent: petroleum ether/ethyl acetate=3/1) as a solid: 96% de (HPLC conditions: Chiralcel AS-H column, hexane/i-PrOH=95/5, 0.5 mL/min, λ=214 nm, t$_R$(minor)=23.0 min, t$_R$(major)=24.5 min); [α]$_D^{20}$=−47.9 (c=1.24, CHCl$_3$); m.p. 103-104° C. (EtOAc/n-hexane); $^1$H NMR (300 MHz, CDCl$_3$) δ 5.27-5.14 (m, 3 H), 5.14-5.01 (m, 2 H), 4.58 (d, J=9.9 Hz, 1 H), 4.25 (dd, J$_1$=12.5 Hz, J$_2$=5.0 Hz, 1 H), 4.13 (dd, J$_1$=12.2 Hz, J$_2$=2.0 Hz, 1 H), 3.71-3.62 (m, 1 H), 3.35 (ddd, J$_1$=13.8 Hz, J$_2$=7.5 Hz, J$_3$=2.3 Hz, 1 H), 3.24 (ddd, J$_1$=13.8 Hz, J$_2$=6.5 Hz, J$_3$=3.0 Hz, 1 H), 2.08 (s, 3 H, Me), 2.07 (s, 3 H, Me), 2.03 (s, 3 H, Me), 2.02 (s, 3 H, Me), 2.12-1.94 (m, 1 H, CH), 1.82-1.60 (m, 5 H, CH$_2$×2 and one proton of CH$_2$), 1.40-1.00 (m, 5 H, CH$_2$×2 and one proton of CH$_2$); $^{13}$C NMR (75 Hz, CDCl$_3$) δ 203.7, 170.5, 170.0, 169.2, 98.5, 88.8, 82.7, 75.7, 73.8, 69.7, 68.1, 61.9, 37.2, 33.0, 32.9, 30.1, 25.9, 25.7, 20.6, 20.5, 20.4; IR (KBr) ν (cm$^{-1}$) 2926, 2852, 1953, 1756, 1448, 1371, 1225, 1040; MS (ESI, m/z) 516 (M+NH$_4^+$); Anal. Calcd. for C$_{24}$H$_{34}$O$_9$S (%): C, 57.81; H, 6.87; Found: C, 58.03; H 6.82.

EXAMPLE 14

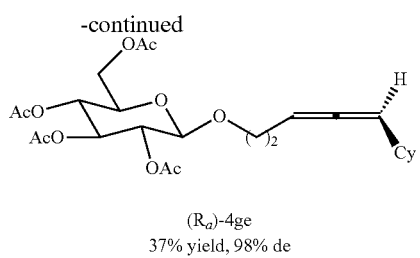

($R_a$)-4ge
37% yield, 98% de

Following the procedure of Example 1. The reaction of CuBr$_2$ (44.7 mg, 0.2 mmol), 1g (402.0 mg, 1.0 mmol), (S)-3a (306.1 mg, 1.2 mmol), and 2e (157.2 mg, 1.4 mmol) in dioxane (3.0 mL) afforded ($R_a$)-4ge (183.2 mg, 37%) (eluent: petroleum ether/ethyl acetate=2.5/1) as a solid: 98% de (HPLC conditions: Chiralcel IC column, hexane/i-PrOH=96/4, 0.4 mL/min, λ=214 nm, $t_R$(minor)=76.6 min, $t_R$(major)=78.3 min); $[α]_D^{20}$=−47.8 (c=1.38, CHCl$_3$); m.p. 86-87° C. (DCM/n-hexane); $^1$H NMR (300 MHz, CDCl$_3$) δ 5.21 (t, J=9.5 Hz, 1 H), 5.14-4.94 (m, 4 H), 4.53 (d, J=8.1 Hz, 1 H), 4.28 (dd, J$_1$=12.3 Hz, J$_2$=4.8 Hz, 1 H), 4.13 (dd, J$_1$=12.3 Hz, J$_2$=2.4 Hz, 1 H), 3.92 (dt, J$_1$=9.6 Hz, J$_2$=6.9 Hz, 1 H), 3.71 (ddd, J$_1$=10.1 Hz, J$_2$=4.8 Hz, J$_1$=2.4 Hz, 1 H), 3.55 (dt, J$_1$=9.6 Hz, J$_2$=7.2 Hz, 1 H), 2.32-2.20 (m, 2 H, CH$_2$), 2.09 (s, 3 H, Me), 2.05 (s, 3 H, Me), 2.03 (s, 3 H, Me), 2.01 (s, 3 H, Me), 2.13-1.88 (m, 1 H, CH), 1.80-1.58 (m, 5 H, CH$_2$×2 and one proton of CH$_2$), 1.37-0.97 (m, 5 H, CH$_2$×2 and one proton of CH$_2$); $^{13}$C NMR (75 Hz, CDCl$_3$) δ 203.2, 170.6, 170.2, 169.3, 169.2, 100.7, 97.4, 87.4, 72.7, 71.6, 71.1, 69.7, 68.2, 61.8, 36.9, 32.9, 32.8, 29.3, 26.0, 25.8, 20.6, 20.5, 20.4; IR (KBr) ν (cm$^{-1}$) 2926, 2852, 1959, 1757, 1448, 1369, 1225, 1170, 1040; MS (ESI, m/z) 514 (M+NH$_4^+$); Anal. Calcd. for C$_{25}$H$_{36}$O$_{10}$ (%): C, 60.47; H, 7.31; Found: C, 60.54; H, 7.25.

EXAMPLE 15

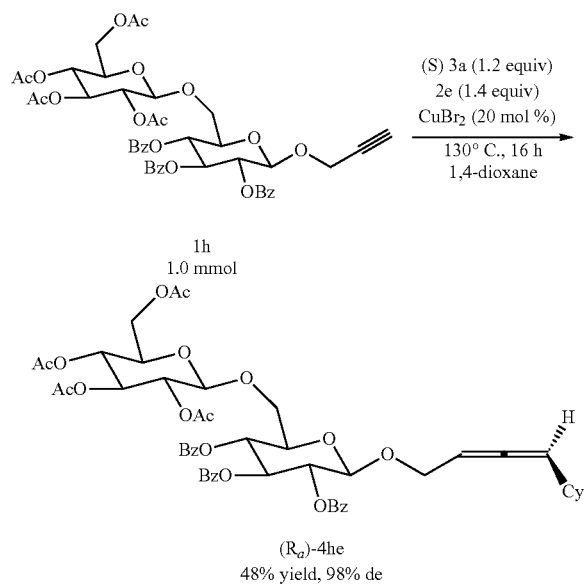

1h
1.0 mmol ($R_a$)-4he
48% yield, 98% de

Following the procedure of Example 1. The reaction of CuBr$_2$ (44.9 mg, 0.2 mmol), 1h (862.1 mg, 1.0 mmol), (S)-3a (304.4 mg, 1.2 mmol), and 2e (157.5 mg, 1.4 mmol) in dioxane (3.0 mL) afforded (R)-4he (456.7 mg, 48%) (eluent: petroleum ether/ethyl acetate=1.5/1) as a syrup: 98% de (HPLC conditions: (Supercritical Fluid Chromatography) Chiralcel IA column, CO$_2$/i-PrOH=80/20, 1.5 mL/min, λ=214 nm, $t_R$(minor)=8.3 min, $t_R$(major)=14.2 min); $[α]_D^{20}$=−13.8 (c=1.21, CHCl$_3$); NMR (300 MHz, CDCl$_3$) δ 7.98-7.88 (m, 4 H, ArH), 7.84-7.78 (m, 2 H, ArH), 7.55-7.45 (m, 2 H, ArH), 7.43-7.32 (m, 5 H, ArH), 7.28-7.20 (m, 2 H, ArH), 5.88 (t, J=9.6 Hz, 1 H), 5.51 (dd, J$_1$=9.6 Hz, J$_2$=8.1 Hz, 1 H), 5.41 (t, J=9.8 Hz, 1 H), 5.26-5.12 (m, 3 H), 5.11-4.98 (m, 2 H), 4.94 (d, J=7.8 Hz, 1 H), 4.65 (d, J=7.8 Hz, 1 H), 4.43-4.33 (m, 1 H), 4.29-4.12 (m, 2 H), 4.10-3.97 (m, 3 H), 3.78 (dd, J=18.8 Hz, J=11.3 Hz, 1 H), 3.74-3.65 (m, 1 H), 2.09 (s, 3 H, Me), 2.01 (s, 3 H, Me), 2.00 (s, 3 H, Me), 1.99 (s, 3 H, Me), 2.12-1.85 (m, 1 H, CH), 1.79-1.57 (m, 5 H, CH$_2$×2 and one proton of CH$_2$), 1.34-0.95 (m, 5 H, CH$_2$×2 and one proton of CH$_2$); $^{13}$C NMR (75 Hz, CDCl$_3$) δ 204.1, 170.3, 170.0, 169.2, 169.1, 165.5, 165.1, 164.8, 133.4. 133.02, 132.99, 129.6, 129.54, 129.47, 129.1, 128.5, 128.4, 128.3, 128.11, 128.05, 100.6, 99.2, 98.2, 88.2, 73.5, 72.8, 72.6, 71.6, 71.5, 70.9, 69.5, 68.2, 68.0, 67.7, 61.6, 36.5, 32.8, 32.5, 25.8, 25.7, 25.6, 20.5, 20.4, 20.3; IR (neat) ν (cm$^{-1}$) 3063, 2927, 2852, 1959, 1754, 1739, 1602, 1452, 1369, 1284, 1251, 1224, 1176, 1094, 1069, 1037; MS (MALDI, m/z) 995 (M+K$^+$) 979 (M+Na$^+$); Anal. Calcd. for C$_{51}$H$_{56}$O$_{18}$ (%): C, 64.01; H, 5.90; Found: C, 64.00; H, 5.80.

EXAMPLE 16

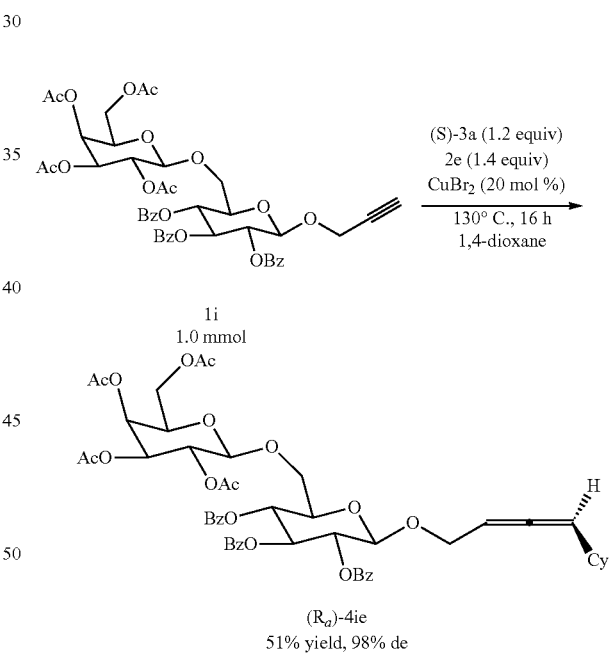

1i
1.0 mmol ($R_a$)-4ie
51% yield, 98% de

Following the procedure of Example 1. The reaction of CuBr$_2$ (45.0 mg, 0.2 mmol), 1i (861.1 mg, 1.0 mmol), (5)-3a (304.2 mg, 1.2 mmol), and 2e (157.2 mg, 1.4 mmol) in dioxane (3.0 mL) afforded ($R_a$)-4ie (492.2 mg, 51%) (eluent: petroleum ether/ethyl acetate=1.5/1) as a syrup: 98% de (HPLC conditions: (Supercritical Fluid Chromatography) Chiralcel IA column, CO$_2$/i-PrOH=70/30, 1.5 mL/min, λ=214 nm, $t_R$(minor)=4.5 min, $t_R$(major)=6.1 min); $[α]_D^{20}$=−13.5 (c=1.12, CHCl$_3$); $^1$H NMR (300 MHz, CDCl$_3$) δ 7.80-7.88 (m, 4 H, ArH), 7.85-7.78 (m, 2 H, ArH), 7.55-7.20 (m, 9 H, ArH), 5.88 (t, J=9.8 Hz, 1 H), 5.51 (dd, J$_1$=9.8 Hz, J$_2$=8.0 Hz, 1 H), 5.46-5.36 (m, 2 H), 5.26 (dd, $J_1$=10.4 Hz, $J_2$=8.0 Hz, 1 H), 5.20-5.12 (m, 2 H), 5.03 (dd, $J_1$=10.4 Hz, $J_2$=3.5 Hz, 1 H), 4.95 (d, J=7.8 Hz, 1 H), 4.62 (d, J=7.8 Hz, 1 H), 4.44-4.34 (m, 1 H), 4.25-3.97 (m, 5 H), 3.92 (t, J=6.5 Hz, 1 H), 3.79 (dd, $J_1$=10.8 Hz, $J_2$=7.5 Hz, 1 H), 2.110 (s, 3 H, Me), 2.107 (s, 3 H, Me), 2.01 (s, 3 H, Me), 1.98 (s, 3 H, Me), 2.18-1.85 (m, 1 H, CH), 1.79-1.57 (m, 5 H, $CH_2 \times 2$ and one proton of $CH_2$), 1.34-0.95 (m, 5 H, $CH_2 \times 2$ and one proton of $CH_2$); $^{13}C$ NMR (75 Hz, $CDCl_3$) δ 204.1, 170.1, 170.0, 169.9, 169.2, 165.5, 165.1, 164.8, 133.4, 133.02, 132.98, 129.5, 129.4, 129.0, 128.5, 128.4, 128.3, 128.1, 128.0, 101.0, 99.2, 98.2, 88.2, 73.5, 72.8, 71.5, 70.7, 70.4, 69.5, 68.4, 68.2, 67.7, 66.8, 61.0, 36.4, 32.8, 32.5, 25.8, 25.7, 25.6, 20.6, 20.4, 20.33, 20.28; IR (neat) ν ($cm^1$) 3066, 2927, 2852, 1959, 1740, 1602, 1451, 1370, 1281, 1255, 1218, 1177, 1090, 1069; MS (MALDI, m/z) 979 ($M+Na^+$); Anal. Calcd. for $C_{51}H_{56}O$ (%): C, 64.01; H, 5.90; Found: C, 64.04; H, 5.88.

EXAMPLE 17

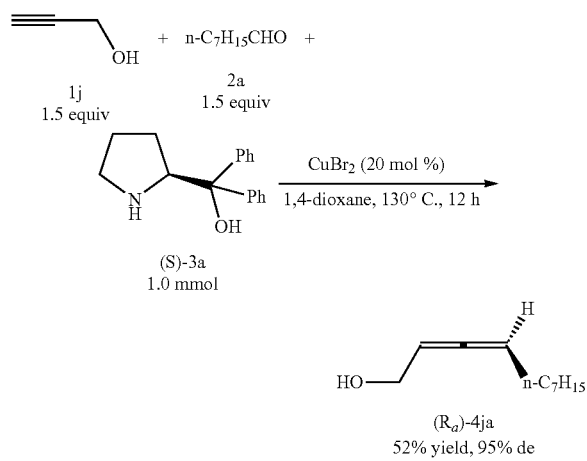

(S)-3a
1.0 mmol ($R_a$)-4ja
52% yield, 95% de

To a flame-dried Schlenk tube with a polytetrafluoroethylene plug were added $CuBr_2$ (44.7 mg, 0.2 mmol), (S)-3a (253.1 mg, 1.0 mmol), 1j (84.3 mg, 1.5 mmol)/dioxane (1.5 mL), and 2a (192.4 mg, 1.5 mmol)/dioxane (1.5 mL) sequentially under nitrogen atmosphere. The Schlenk tube was then sealed by screwing the polytetrafluoroethylene plug tightly with the outlet connected to the vacuum line with a nitrogen flow being closed. The reaction was complete after being stirred at 130° C. for 12 h as monitored by TLC (eluent: petroleum ether/ethyl acetate=10/1). Then the resulting mixture was diluted with ether (30 mL), and washed with an aqueous solution of hydrochloric acid (3 M, 20 mL). The organic layer was separated, and the aqueous layer was extracted with ether (20 mL). The combined organic layer was washed with brine and dried over anhydrous $Na_2SO_4$. After filtration and evaporation, the residue was purified by chromatography (eluent: petroleum ether/ethyl acetate=8/1) on silica gel to afford ($R_a$)-4ja (86.8 mg, 52%) as a liquid: 95% ee (HPLC conditions: Chiralcel AS-H column, hexane/i-PrOH=98/2, 0.6 mL/min, λ=214 nm, $t_R$(major)=10.9 min, $t_R$(minor)=11.8 min); $[α]_D^{20}$=−68.9 (c=1.01, $CHCl_3$); (reported value: 97% ee; $[α]_D^{20}$=−66.1 (c=1.03, $CHCl_3$)); $^1H$ NMR (300 MHz, $CDCl_3$) δ 5.37-5.24 (m, 2 H, CH=C=CH), 4.17-4.07 (m, 2 H, $OCH_2$), 2.08-1.96 (m, 2 H, $CH_2$), 1.57 (t, J=4.8 Hz, 1 H, OH), 1.48-1.20 (m, 10 H, $CH_2 \times 5$), 0.88 (t, J=6.8 Hz, 3 H, Me); $^{13}C$ NMR (75 MHz, $CDCl_3$) δ 202.9, 94.0, 91.7, 60.8, 31.8, 29.08, 29.07, 29.0, 28.6, 22.6, 14.1; IR (neat) ν ($cm^{-1}$) 3336, 2956, 2926, 2855, 1963, 1465, 1376, 1013; MS (EI): m/z (%) 168 ($M^+$, 0.04), 55 (100). (reference: J. Ye, W. Fan, S. Ma, *Chem. Eur. J.* 2013, 19, 716).

EXAMPLE 18

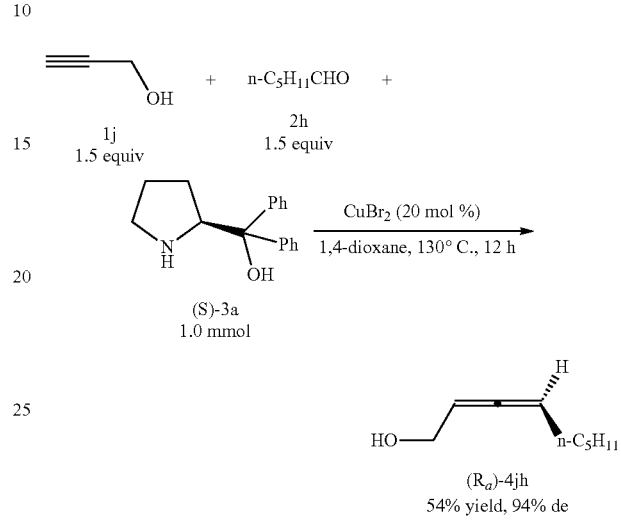

(S)-3a
1.0 mmol ($R_a$)-4jh
54% yield, 94% de

Following the procedure of Example 17. The reaction of $CuBr_2$ (44.9 mg, 0.2 mmol), 1j (84.6 mg, 1.5 mmol), (S)-3a (252.6 mg, 1.0 mmol), and 2h (150.2 mg, 1.5 mmol) in dioxane (3.0 mL) afforded ($R_a$)-4jh (75.2 mg, 54%) (eluent: petroleum ether/ethyl acetate=8/1) as a liquid: 94% ee (HPLC conditions: Chiralcel AS-H column, hexane/i-PrOH=100/1, 0.5 mL/min, λ=214 nm, $t_R$(major)=18.9 min, $t_R$(minor)=20.0 min); $[c]_D^{20}$=−78.5 (c=1.11, $CHCl_3$) (reported value: 98% ee; $[α]_D^{21}$=−78.4 (c=1.03, $CHCl_3$)); $^1H$ NMR (300 MHz, $CDCl_3$) δ 5.36-5.23 (m, 2 H, CH=C=CH), 4.11 (dd, $J_1$=5.6 Hz, $J_2$=3.2 Hz, 2 H, $OCH_2$), 2.08-1.96 (m, 2 H, $CH_2$), 1.80 (s, 1 H, OH), 1.49-1.21 (m, 6 H, $CH_2 \times 3$), 0.89 (t, J=7.1 Hz, 3 H, Me); $^{13}C$ NMR (75 MHz, $CDCl_3$) δ 203.0, 93.9, 91.6, 60.7, 31.2, 28.7, 28.6, 22.4, 14.0; IR (neat) ν ($cm^{-1}$) 3337, 2957, 2927, 2857, 1963, 1466; MS (EI): m/z (%) 122 (($M-H_2O)^+$, 0.68), 55 (100). (reference: J. Ye, W. Fan, S. Ma, *Chem. Eur. J.* 2013, 19, 716).

EXAMPLE 19

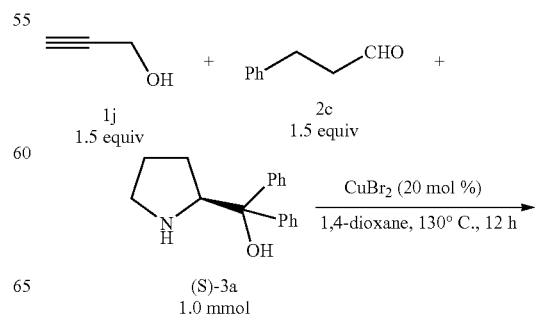

(S)-3a
1.0 mmol

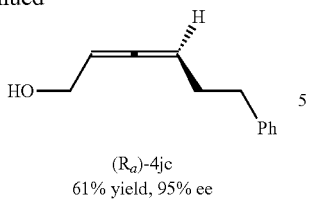

(R$_a$)-4jc
61% yield, 95% ee

Following the procedure of Example 17. The reaction of CuBr$_2$ (45.0 mg, 0.2 mmol), 1j (84.2 mg, 1.5 mmol), (S)-3a (253.1 mg, 1.0 mmol), and 2c (201.4 mg, 1.5 mmol) in dioxane (3.0 mL) afforded (R$_a$)-4jc (106.1 mg, 61%) (eluent: petroleum ether/ethyl acetate=8/1 to petroleum ether/ethyl acetate=5/1) as a liquid: 95% ee (HPLC conditions: Chiralcel AS-H column, hexane/i-PrOH=100/1, 1.0 mL/min, λ=214 nm, t$_R$(major)=22.4 min, t$_R$(minor)=24.4 min); [α]$_D^{20}$=−38.0 (c=0.89, CHCl$_3$) (reported value: 96% ee; [α]$_D^{2o}$=−38.7 (c=1.05, CHCl$_3$)); $^1$H NMR (300 MHz, CDCl$_3$) δ 7.36-7.13 (m, 5 H, ArH), 5.35-5.21 (m, 2 H, CH═C═CH), 4.04-3.90 (m, 2 H, OCH$_2$), 2.83-2.64 (m, 2 H, CH$_2$), 2.46-2.24 (m, 2 H, CH$_2$), 1.62 (s, 1 H, OH); $^{13}$C NMR (75 MHz, CDCl$_3$) δ 203.2, 141.4, 128.4, 128.2, 125.9, 92.9, 92.1, 60.4, 35.0, 29.9; IR (neat) ν (cm$^{-1}$) 3366, 3084, 3062, 3026, 2923, 2856, 1962, 1603, 1496, 1453, 1062, 1011; MS (EI) m/z (%): 174 (M$^+$, 0.03), 156 ((M−H$_2$O)$^+$, 41.67), 91 (100). (reference: J. Ye, W. Fan, S. Ma, *Chem. Eur. J.* 2013, 19, 716).

EXAMPLE 20

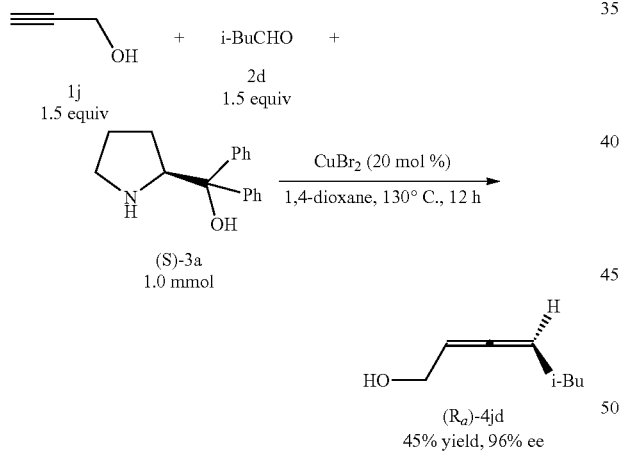

(R$_a$)-4jd
45% yield, 96% ee

Following the procedure of Example 17. The reaction of CuBr$_2$ (44.6 mg, 0.2 mmol), 1j (84.5 mg, 1.5 mmol), (S)-3a (253.6 mg, 1.0 mmol), and 2d (129.5 mg, 1.5 mmol) in dioxane (3.0 mL) afforded (R$_a$)-4jd (57.3 mg, 45%) (eluent: petroleum ether/ethyl acetate=8/1) as a liquid: 96% ee (HPLC conditions: Chiralcel AD-H column, hexane/i-PrOH=200/1, 1.0 mL/min, λ=214 nm, t$_R$(major)=18.7 min, t$_R$(minor)=22.0 min); [α]$_D^{20}$=−79.9 (c=0.955, CHCl$_3$) (reported value: 98% ee; [α]$_D^{22}$=−80.3 (c=1.01, CHCl$_3$)); $^1$H NMR (300 MHz, CDCl$_3$) δ 5.35-5.19 (m, 2 H, CH═C═CH), 4.11 (dd, J$_1$=5.9 Hz, J$_2$=2.9 Hz, 2 H, OCH$_2$), 1.97-1.89 (m, 2 H, CH$_2$), 1.76-1.57 (m, 2 H, CH and OH), 0.93 (d, J=6.6 Hz, 6 H, Me×2); $^{13}$C NMR (75 MHz, CDCl$_3$) δ 203.6, 92.3, 91.0, 60.8, 38.1, 28.4, 22.12, 22.10; IR (neat) ν (cm$^{-1}$) 3338, 2956, 2926, 2893, 2870, 1962, 1466, 1384, 1367, 1056, 1014; MS (EI) m/z (%): 126 (M$^+$, 0.10), 108 ((M−H$_2$O)$^+$, 31.12), 55 (100). (reference: J. Ye, W. Fan, S. Ma, *Chem. Eur J.* 2013, 19, 716).

EXAMPLE 21

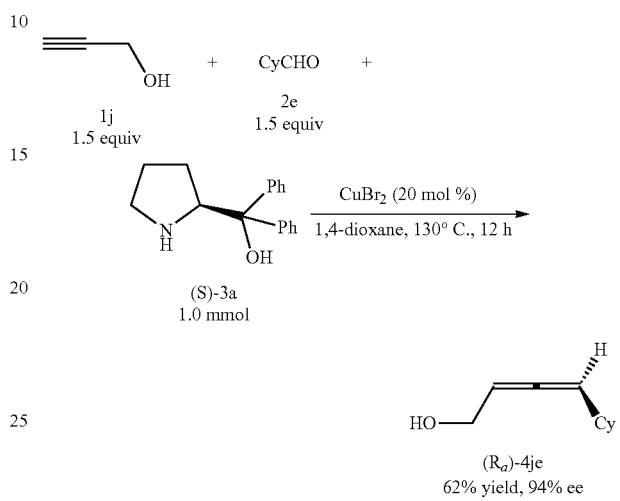

(R$_a$)-4je
62% yield, 94% ee

Following the procedure of Example 17. The reaction of CuBr$_2$ (44.7 mg, 0.2 mmol), 1j (84.8 mg, 1.5 mmol), (S)-3a (252.2 mg, 1.0 mmol), and 2e (168.2 mg, 1.5 mmol) in dioxane (3.0 mL) afforded (R$_a$)-4je (94.2 mg, 62%) (eluent: petroleum ether/ethyl acetate=8/1) as a liquid: 94% ee (HPLC conditions: Chiralcel AS-H column, hexane/i-PrOH=98/2, 0.6 mL/min, λ=214 nm, t$_R$(major)=15.7 min, t$_R$(minor)=18.6 min); [α]$_D^{20}$=−98.1 (c=1.045, CHCl$_3$) (reported value: 99% ee; [α]$_D^{22}$=−100.3 (c=1.00, CHCl$_3$)); $^1$H NMR (300 MHz, CDCl$_3$) δ 5.41-5.25 (m, 2 H, CH═C═CH), 4.10 (dd, J$_1$=5.7 Hz, J$_2$=3.0 Hz, 2 H, OCH$_2$), 2.08-1.93 (m, 1 H, CH from Cy), 1.88-1.58 (m, 6 H, OH and five protons from Cy), 1.37-1.00 (m, 5 H, five protons from Cy); $^{13}$C NMR (75 MHz, CDCl$_3$) δ 201.8, 99.9, 92.6, 60.8, 37.0, 33.0, 32.9, 26.0, 25.9; IR (neat) ν (cm$^{-1}$) 3331, 2924, 2851, 1961, 1448, 1412, 1011; MS (EI) m/z (%): 152 (M$^+$, 0.38), 134 ((M−H$_2$O)$^+$, 6.78), 55 (100). (reference: J. Ye, W. Fan, S. Ma, *Chem. Eur J.* 2013, 19, 716).

EXAMPLE 22

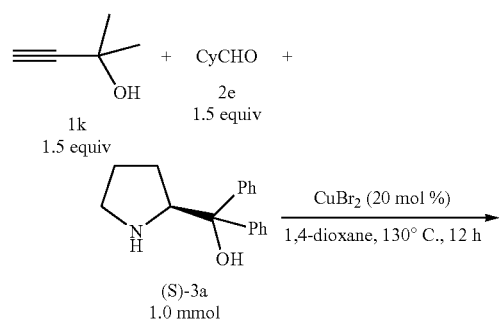

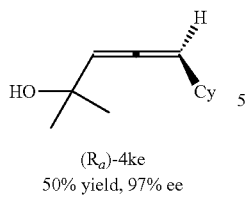

(R$_a$)-4ke
50% yield, 97% ee

Following the procedure of Example 17. The reaction of CuBr$_2$ (44.7 mg, 0.2 mmol), 1k (126.8 mg, 1.5 mmol), (S)-3a (253.2 mg, 1.0 mmol), and 2e (168.6 mg, 1.5 mmol) in dioxane (3.0 mL) afforded (R$_a$)-4ke (89.3 mg, 50%) (eluent: petroleum ether/ethyl acetate=12/1) as a liquid: 97% ee (HPLC conditions: Chiralcel AD-H column, hexane/i-PrOH=95/5, 0.6 mL/min, λ=214 nm, t$_R$(major)=8.9 min, t$_R$(minor)=10.2 min); [α]$_D^{20}$=−99.2 (c=0.97, CHCl$_3$) (reported value: 97% ee; [α]$_D^{20}$=−99.5 (c=1.15, CHCl$_3$)); $^1$H NMR (300 MHz, CDCl$_3$) δ 5.38-5.26 (m, 2 H, CH=C=CH), 2.07-1.92 (m, 1 H, CH from Cy), 1.84-1.59 (m, 6 H, OH and five protons from Cy), 1.34 (s, 6 H, Me×2), 1.37-0.98 (m, 5 H, five protons from Cy); $^{13}$C NMR (75 MHz, CDCl$_3$) δ 199.1, 102.1, 101.0, 69.5, 37.2, 33.02, 32.99, 30.0, 29.9, 26.03, 26.00; IR (neat) ν (cm$^{-1}$) 3358, 2974, 2925, 2851, 1960, 1448, 1373, 1361, 1228, 1149; MS (EI) m/z (%): 180 (M$^+$, 0.29), 165 (M−Me)$^+$, 3.81), 59 (100). (reference: J. Ye, S. Li, B. Chen, W. Fan, J. Kuang, J. Liu, Y. Liu, B. Miao, B. Wan, Y. Wang, X. Xie, Q. Yu, W. Yuan, S. Ma, Org. Lett. 2012, 14, 1346).

EXAMPLE 23

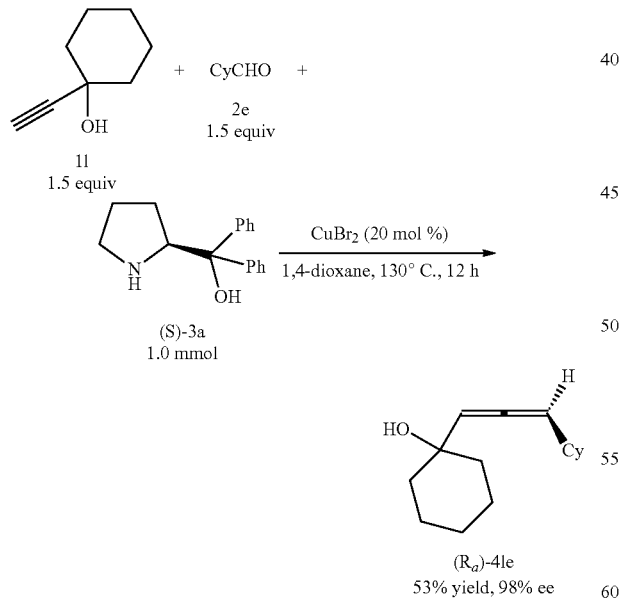

Following the procedure of Example 17. The reaction of CuBr$_2$ (44.9 mg, 0.2 mmol), 1l (186.8 mg, 1.5 mmol), (S)-3a (252.7 mg, 1.0 mmol), and 2e (168.2 mg, 1.5 mmol) in dioxane (3.0 mL) afforded (R$_a$)-4le (115.6 mg, 53%) (eluent: petroleum ether/ethyl acetate=20/1) as a liquid: 98% ee (HPLC conditions: Chiralcel AD-H column, hexane/i-PrOH=100/1, 0.5 mL/min, λ=214 nm, t$_R$(major)=23.5 min, t$_R$(minor)=26.2 min); [α]$_D^{20}$=−106.6 (c=1.21, CHCl$_3$) (reported value: 96% ee; [α]$_D^{20}$=−108.6 (c=0.98, CHCl$_3$)); $^1$H NMR (300 MHz, CDCl$_3$) δ 5.31 (d, J=4.2 Hz, 2 H, CH=C=CH), 2.08-1.90 (m, 1 H, CH from Cy), 1.87-1.40 (m, 15 H), 1.40-1.00 (m, 6 H); $^{13}$C NMR (75 MHz, CDCl$_3$) δ 199.9, 101.3, 100.8, 70.4, 38.4, 38.2, 37.2, 33.1, 33.0, 26.00, 25.97, 25.5, 22.4; IR (neat) ν (cm$^{-1}$) 3373, 2926, 2851, 1960, 1448, 1347, 1262, 1242, 1146, 1056, 1034; MS (EI) m/z (%): 220 (M$^+$, 0.69), 99 (100). (reference: J. Ye, S. Li, B. Chen, W. Fan, J. Kuang, J. Liu, Y. Liu, B. Miao, B. Wan, Y. Wang, X. Xie, Q. Yu, W. Yuan, S. Ma, Org. Lett. 2012, 14, 1346).

EXAMPLE 24

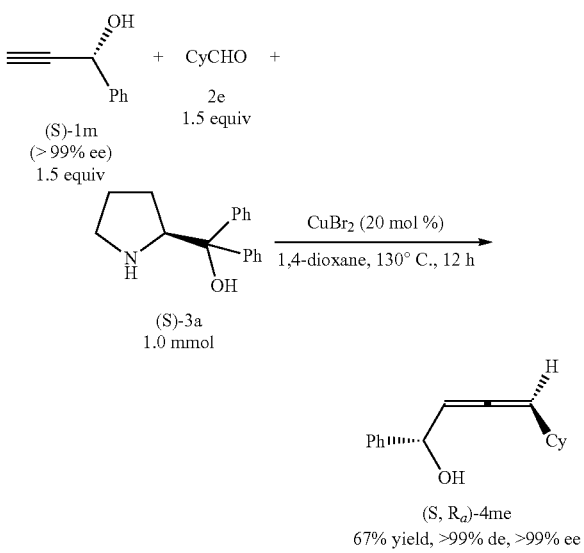

(S, R$_a$)-4me
67% yield, >99% de, >99% ee

Following the procedure of Example 17. The reaction of CuBr$_2$ (44.7 mg, 0.2 mmol), (S)-1m (197.6 mg, 1.5 mmol), (S)-3a (252.7 mg, 1.0 mmol), and 2e (168.3 mg, 1.5 mmol) in dioxane (3.0 mL) afforded (S,R$_a$)-4me (152.0 mg, 67%) (eluent: petroleum ether/ethyl acetate=12/1) as a liquid: >99% de, >99% ee (major isomer) (HPLC conditions: Chiralcel OD-H column, hexane/i-PrOH=98/2, 1.0 mL/min, λ=214 nm, t$_R$(major)=19.4 min; [α]$_D^{20}$=−69.7 (c=1.24, CHCl$_3$) (reported value: 92% de, >99% ee; [α]$_D^{20}$=−60.7 (c=1.02, CHCl$_3$)); $^1$H NMR (300 MHz, CDCl$_3$) δ 7.42-7.21 (m, 5 H, ArH), 5.47-5.38 (m, 1 H, one proton from HC=C=CH), 5.38-5.30 (m, 1 H, one proton from HC=C=CH), 5.21 (d, J=5.4 Hz, 1 H, PhCH), 2.33 (s, 1 H, OH), 2.07-1.91 (m, 1 H, CH from Cy), 1.80-1.56 (m, 5 H, five protons from Cy), 1.35-0.96 (m, 5 H, five protons from Cy); $^{13}$C NMR (75 MHz, CDCl$_3$) δ 201.2, 143.2, 128.3, 127.5, 126.0, 100.9, 96.9, 72.3, 37.1, 32.9, 26.0, 25.9; IR (neat) ν (cm$^{-1}$) 3365, 3063, 3029, 2924, 2850, 1960, 1599, 1489, 1449, 1015; MS (EI) m/z (%): 228 (M$^+$, 2.53), 107 (100). (reference: J. Ye, S. Li, B. Chen, W. Fan, J. Kuang, J. Liu, Y. Liu, B. Miao, B. Wan, Y. Wang, X. Xie, Q. Yu, W. Yuan, S. Ma, Org. Lett. 2012, 14, 1346).

EXAMPLE 25

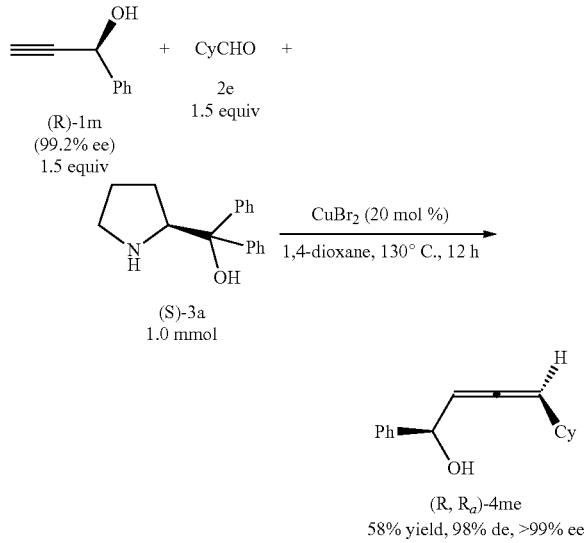

Following the procedure of Example 17. The reaction of CuBr$_2$ (45.0 mg, 0.2 mmol), (R)-1m (198.5 mg, 1.5 mmol), (S)-3a (253.7 mg, 1.0 mmol), and 2e (168.1 mg, 1.5 mmol) in dioxane (3.0 mL) afforded (R,R$_a$)-4me (133.3 mg, 58%) (eluent: petroleum ether/ethyl acetate=12/1) as a liquid: 98% de, >99% ee (major isomer) (HPLC conditions: Chiralcel OD-H column, hexane/i-PrOH=98/2, 1.0 mL/min, λ=214 nm, t$_R$(major)=11.1 min; $[α]_D^{20}$=−52.6 (c=0.98, CHCl$_3$) (reported value: 94% de, 97% ee; $[α]_D^{20}$=−56.8 (c=0.98, CHCl$_3$)); NMR (300 MHz, CDCl$_3$) δ 7.40-7.29 (m, 4 H, ArH), 7.29-7.21 (m, 1 H, ArH), 5.47-5.38 (m, 1 H, one proton from HC=C=CH), 5.37-5.30 (m, 1 H, one proton from HC=C=CH), 5.18 (dd, J$_1$=5.9 Hz, J$_2$=2.6 Hz, 1 H. PhCH), 2.30 (s, 1 H, OH), 2.07-1.93 (m, 1 H, CH from Cy), 1.80-1.56 (m, 5 H, five protons from Cy), 1.36-0.98 (m, 5 H, five protons from Cy); $^{13}$C NMR (75 MHz, CDCl$_3$) δ 200.9, 143.1, 128.3, 127.5, 126.1, 101.2, 97.0, 72.1, 37.1, 32.9, 26.0, 25.9; IR (neat) ν (cm$^{-1}$) 3373, 3063, 3029, 2924, 2850, 1961, 1599, 1493, 1449, 1014; MS (EI) m/z (%): 228 (M$^+$, 2.17), 107 (100). (reference: J. Ye, S. Li, B. Chen, W. Fan, J. Kuang, J. Liu, Y. Liu, B. Miao, B. Wan, Y. Wang, X. Xie, Q. Yu, W. Yuan, S. Ma, *Org. Lett.* 2012, 14, 1346).

EXAMPLE 26

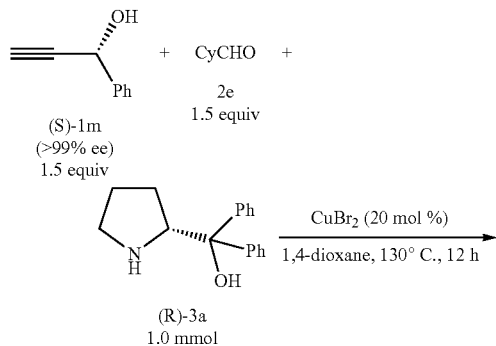

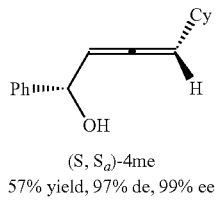

(S, S$_a$)-4me
57% yield, 97% de, 99% ee

Following the procedure of Example 17. The reaction of CuBr$_2$ (45.0 mg, 0.2 mmol), (S)-1m (198.2 mg, 1.5 mmol), (R)-3a (253.8 mg, 1.0 mmol), and 2e (167.9 mg, 1.5 mmol) in dioxane (3.0 mL) afforded (S,S$_a$)-4me (131.5 mg, 57%) (eluent: petroleum ether/ethyl acetate=12/1) as a liquid: 97% de, 99% ee (major isomer) (HPLC conditions: Chiralcel OD-H column, hexane/i-PrOH=98/2, 1.0 mL/min, λ=214 nm, t$_R$(minor)=11.7 min, t$_R$(major)=16.1 min; $[α]_D^{20}$=+56.6 (c=1.34, CHCl$_3$) (reported value: 89% de, >99% ee; $[α]_D^{20}$=+54.7 (c=1.17, CHCl$_3$)); $^1$H NMR (300 MHz, CDCl$_3$) δ 7.41-7.21 (m, 5 H, ArH), 5.47-5.38 (m, 1 H, one proton from HC=C=CH), 5.37-5.30 (m, 1 H, one proton from HC=C=CH), 5.18 (dd, J$_1$=5.7 Hz, J$_2$=2.4 Hz, 1 H, PhCH), 2.33 (s, 1 H, OH), 2.08-1.93 (m, 1 H, CH from Cy), 1.80-1.56 (m, 5 H, five protons from Cy), 1.36-0.98 (m, 5 H, five protons from Cy); $^{13}$C NMR (75 MHz, CDCl$_3$) δ 200.9, 143.1, 128.3, 127.5, 126.1, 101.2, 97.0, 72.1, 37.0, 32.9, 26.0, 25.9; IR (neat) ν (cm$^{-1}$) 3365, 3062, 3029, 2924, 2850, 1961, 1602, 1492, 1449, 1014; MS (EI) m/z (%): 228 (M$^+$, 1.93), 107 (100). (reference: J. Ye, S. Li, B. Chen, W. Fan, J. Kuang, J. Liu, Y. Liu, B. Miao, B. Wan, Y. Wang, X. Xie, Q. Yu, W. Yuan, S. Ma, *Org. Lett.* 2012, 14, 1346).

EXAMPLE 27

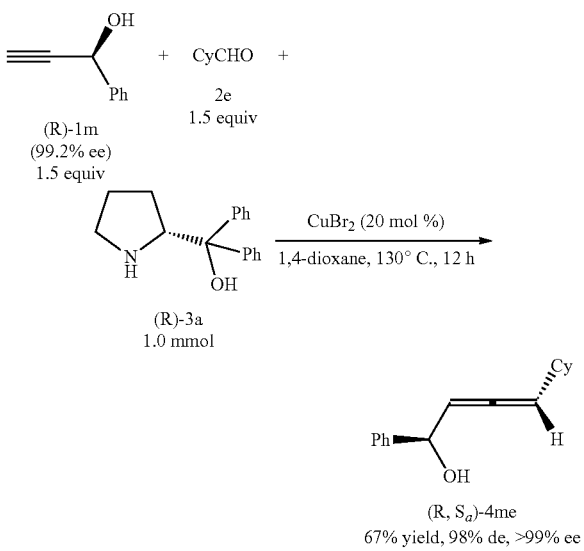

(R, S$_a$)-4me
67% yield, 98% de, >99% ee

Following the procedure of Example 17. The reaction of CuBr$_2$ (45.0 mg, 0.2 mmol), (R)-1m (197.6 mg, 1.5 mmol), (R)-3a (254.0 mg, 1.0 mmol), and 2e (169.2 mg, 1.5 mmol) in dioxane (3.0 mL) afforded (R,S$_a$)-4me (153.4 mg, 67%) (eluent: petroleum ether/ethyl acetate=12/1) as a liquid: 98% de, >99% ee (major isomer) (HPLC conditions: Chiralcel OD-H column, hexane/i-PrOH=98/2, 1.0 mL/min, λ=214 nm, t$_R$(major)=13.4 min; $[α]_D^{20}$=+73.0 (c=1.165, CHCl$_3$)

(reported value: 93% de, >99% ee; $[\alpha]_D^{20}$=+60.8 (c=0.62, CHCl$_3$)); $^1$H NMR (300 MHz, CDCl$_3$) δ 7.41-7.21 (m, 5 H, ArH), 5.47-5.38 (m, 1 H, one proton from HC=C=CH), 5.37-5.30 (m, 1 H, one proton from HC=C=CH), 5.19 (d, J=5.7 Hz, 1 H, PhCH), 2.40 (s, 1 H, OH), 2.07-1.91 (m, 1 H, CH from Cy), 1.80-1.56 (m, 5 H, five protons from Cy), 1.35-0.97 (m, 5 H, five protons from Cy); $^{13}$C NMR (75 MHz, CDCl$_3$) δ 201.2, 143.2, 128.3, 127.5, 126.0, 100.8, 96.9, 72.3, 37.1, 32.87, 32.85, 26.0, 25.9; IR (neat) ν (cm$^{-1}$) 3358, 3062, 3029, 2924, 2850, 1961, 1602, 1493, 1449, 1015; MS (EI) m/z (%): 228 (M$^+$, 2.23), 107 (100). (reference: J. Ye, S. Li, B. Chen, W. Fan, J. Kuang, J. Liu, Y. Liu, B. Miao, B. Wan, Y. Wang, X. Xie, Q. Yu, W. Yuan, S. Ma, *Org. Lett.* 2012, 14, 1346).

EXAMPLE 28

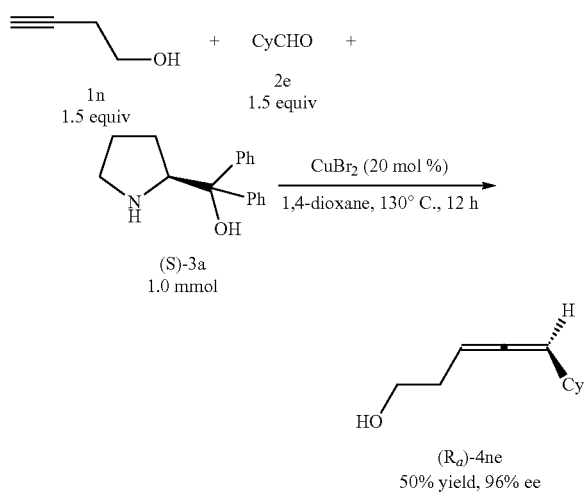

(R$_a$)-4ne
50% yield, 96% ee

Following the procedure of Example 17. The reaction of CuBr$_2$ (45.0 mg, 0.2 mmol), 1n (106.0 mg, 1.5 mmol), (S)-3a (252.6 mg, 1.0 mmol), and 2e (168.4 mg, 1.5 mmol) in dioxane (3.0 mL) afforded (R$_a$)-4ne (83.5 mg, 50%) (eluent: petroleum ether/ethyl acetate=6/1) as a liquid: 96% ee (HPLC conditions: Chiralcel IC column, hexane/i-PrOH=100/1, 0.6 mL/min, λ=214 nm, t$_R$(minor)=20.5 min, t$_R$(major)=22.0 min); $[\alpha]_D^{20}$=-84.5 (c=1.095, CHCl$_3$); $^1$H NMR (300 MHz, CDCl$_3$) δ 5.18-5.07 (m, 2 H, CH=C=CH), 3.70 (t, J=6.3 Hz, 2 H, OCH$_2$), 2.30-2.19 (m, 2 H, CH$_2$), 2.05-1.89 (m, 1 H, CH from Cy), 1.89-1.57 (m, 6 H, OH and five protons from Cy), 1.37-0.98 (m, 5 H, five protons from Cy); $^{13}$C NMR (75 MHz, CDCl$_3$) δ 203.4, 97.7, 88.0, 62.0, 37.1, 33.04, 33.02, 32.4, 26.1, 26.0; IR (neat) ν (cm$^{-1}$) 3340, 2924, 2851, 1961, 1448, 1049; MS (EI) m/z (%): 166 (M$^+$, 6.05), 67 (100); HRMS calcd for C$_{11}$H$_{18}$O [M$^+$]: 166.1358; Found: 166.1365.

EXAMPLE 29

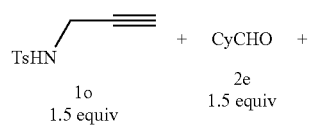

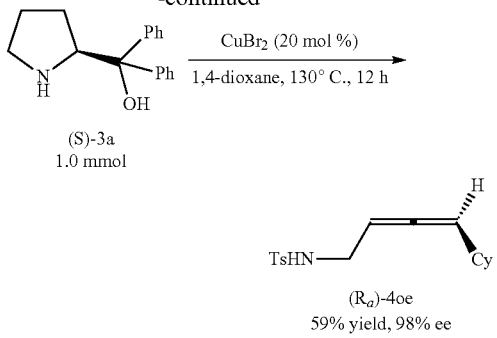

(R$_a$)-4oe
59% yield, 98% ee

Following the procedure of Example 17. The reaction of CuBr$_2$ (45.0 mg, 0.2 mmol), 1o (313.4 mg, 1.5 mmol), (S)-3a (253.9 mg, 1.0 mmol), and 2e (167.8 mg, 1.5 mmol) in dioxane (3.0 mL) afforded (R$_a$)-4oe (180.0 mg, 59%) (eluent: petroleum ether/ethyl acetate=5/1) as a liquid: 98% ee (HPLC conditions: Chiralcel AD-H column, hexane/i-PrOH=95/5, 0.5 mL/min, λ=214 nm, t$_R$(major)=34.1 min, t$_R$(minor)=35.6 min); $[\alpha]_D^{20}$=-102.0 (c=1.05, CHCl$_3$) (reported value: 99% ee; $[\alpha]_D^{20}$=-105.5 (c=1.07, CHCl$_3$)); $^1$H NMR (300 MHz, CDCl$_3$) δ 7.80-7.72 (m, 2 H, ArH), 7.30 (d, J=7.8 Hz, 2 H, ArH), 5.21-5.12 (m, 1 H, one proton of CH=C=CH), 5.11-5.01 (m, 1 H, one proton of CH=C=CH), 4.85 (t, J=5.9 Hz, 1 H, NH), 3.60-3.50 (m, 2 H, NCH$_2$), 2.42 (s, 3 H, CH$_3$), 1.98-1.82 (m, 1 H, CH from Cy), 1.73-1.53 (m, 5 H, five protons from Cy), 1.32-0.89 (m, 5 H, five protons from Cy); $^{13}$C NMR (75 MHz, CDCl$_3$) δ 202.3, 143.3, 137.0, 129.6, 127.0, 100.4, 88.4, 42.0, 36.7, 32.8, 32.7, 25.9, 25.8, 21.4; IR (neat) ν (cm$^{-1}$) 3284, 2924, 2850, 1962, 1598, 1495, 1418, 1329, 1161, 1094; MS (EI) m/z (%): 305 (M$^+$, 1.14), 91 (100). (reference: J. Ye, W. Fan, S. Ma, *Chem. Eur. J.* 2013, 19, 716).

EXAMPLE 30

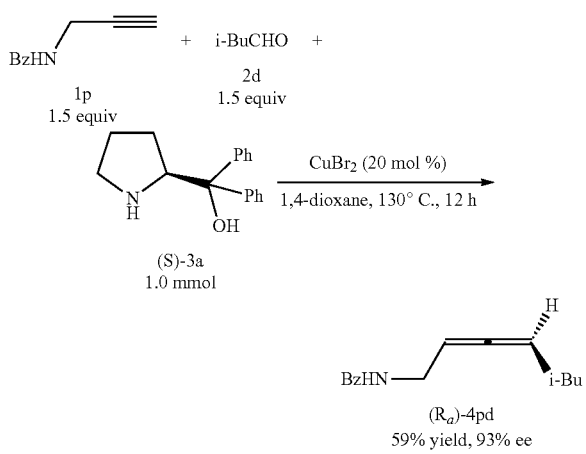

(R$_a$)-4pd
59% yield, 93% ee

Following the procedure of Example 17. The reaction of CuBr$_2$ (44.9 mg, 0.2 mmol), 1p (238.4 mg, 1.5 mmol), (S)-3a (254.3 mg, 1.0 mmol), and 2d (129.9 mg, 1.5 mmol) in dioxane (3.0 mL) afforded (R$_a$)-4pd (136.8 mg, 59%) (eluent: petroleum ether/ethyl acetate=5/1) as a liquid: 93% ee (HPLC conditions: Chiralcel AY-H column, hexane/i-PrOH=90/10, 1.0 mL/min, λ=214 nm, t$_R$(major)=9.8 min, $t_R$(minor)=11.2 min); $[\alpha]_D^{20}$=−92.5 (c=0.78, CHCl$_3$); $^1$H NMR (300 MHz, CDCl$_3$) δ 7.82-7.73 (m, 2 H, ArH), 7.51-7.35 (m, 3 H, ArH), 6.52 (bs, 1 H, NH), 5.30-5.19 (m, 2 H, CH=C=CH), 4.05-3.95 (m, 2 H, NCH$_2$), 1.96-1.86 (m, 2 H, CH$_2$), 1.73-1.55 (m, 1 H, CH), 0.894 (d, J=6.6 Hz, 3 H, Me), 0.891 (d, J=6.6 Hz, 3 H, Me); $^{13}$C NMR (75 MHz, CDCl$_3$) δ 203.8, 167.3, 134.5, 131.3, 128.4, 126.8, 92.9, 87.8, 38.5, 38.0, 28.3, 22.1, 22.0; IR (neat) ν (cm$^{-1}$) 3320, 3064, 2955, 2927, 2869, 1964, 1727, 1644, 1603, 1578, 1538, 1489, 1465, 1308, 1076; MS (EI) m/z (%): 229 (M$^+$, 7.05), 105 (100); HRMS calcd for C$_{15}$H$_{19}$NO [M$^+$]: 229.1467; Found: 229.1469.

EXAMPLE 31

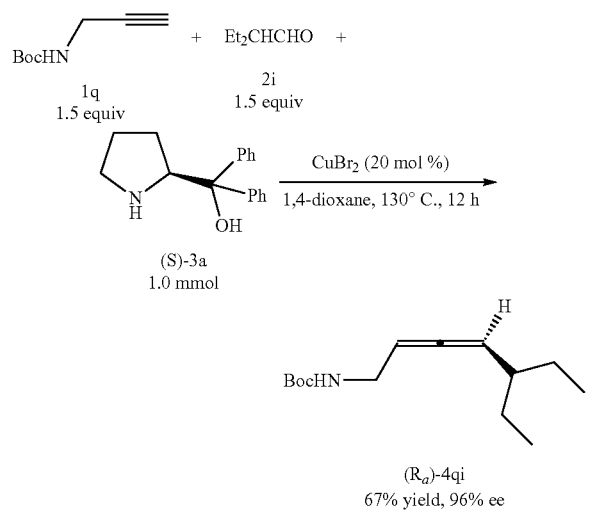

(R$_a$)-4qi
67% yield, 96% ee

Following the procedure of Example 17. The reaction of CuBr$_2$ (44.9 mg, 0.2 mmol), 1q (232.8 mg, 1.5 mmol), (S)-3a (253.2 mg, 1.0 mmol), and 2i (150.6 mg, 1.5 mmol) in dioxane (3.0 mL) afforded (R$_a$)-4qi (160.3 mg, 67%) (eluent: petroleum ether/ethyl acetate=50/1 to petroleum ether/ethyl acetate=20/1) as a liquid: 96% ee (HPLC conditions: Chiralcel OD-H column, hexane/i-PrOH=100/0, 1.0 mL/min, λ=214 nm, $t_R$(minor)=19.7 min, $t_R$(major)=20.4 min); $[\alpha]_D^{20}$=−63.5 (c=1.055, CHCl$_3$); $^1$H NMR (300 MHz, CDCl$_3$) δ 5.22-5.12 (m, 1 H, one proton of CH=C=CH), 5.11-5.03 (m, 1 H, one proton of CH=C=CH), 4.71 (bs, 1 H, NH), 3.77-3.63 (m, 2 H, NCH$_2$), 1.93-1.78 (m, 1 H, CH), 1.53-1.21 (m, 13 H, Me×2 and CH$_2$×2), 0.90 (t, J=7.4 Hz, 3 H, Me), 0.89 (t, J=7.4 Hz, 3 H, Me); $^{13}$C NMR (75 MHz, CDCl$_3$) δ 203.0, 155.6, 97.7, 89.0, 79.1, 42.7, 39.3, 28.3, 27.5, 27.2, 11.6, 11.4; IR (neat) ν (cm$^{-1}$) 3351, 2965, 2931, 2875, 1963, 1698, 1505, 1456, 1392, 1366, 1250, 1172, 1053; MS (EI) m/z (%): 239 (M$^+$, 0.01), 183 ((M−$^t$Bu+H)$^+$, 45.91), 57 (100); HRMS calcd for C$_{14}$H$_{25}$NO$_2$ [M$^+$]: 239.1885; Found: 239.1878.

EXAMPLE 32

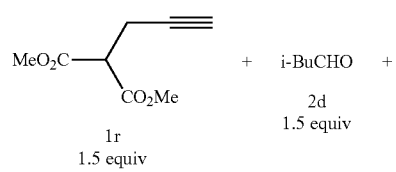

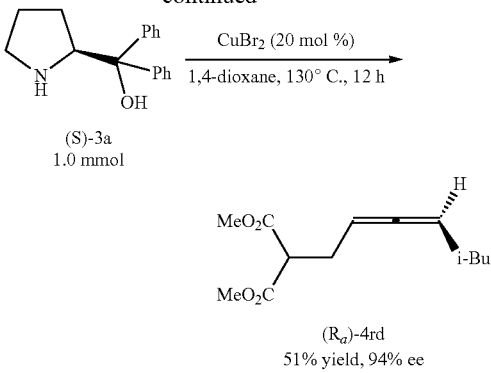

(R$_a$)-4rd
51% yield, 94% ee

Following the procedure of Example 17. The reaction of CuBr$_2$ (45.0 mg, 0.2 mmol), 1r (255.7 mg, 1.5 mmol), (S)-3a (252.5 mg, 1.0 mmol), and 2d (129.6 mg, 1.5 mmol) in dioxane (3.0 mL) afforded (R$_a$)-4rd (121.9 mg, 51%) (eluent: petroleum ether/ethyl acetate=20/1) as a liquid: 94% ee (HPLC conditions: Chiralcel OD-H column, hexane/i-PrOH=100/1, 0.7 mL/min, λ=214 nm, $t_R$(minor)=10.9 min, $t_R$(major)=11.7 min); $[\alpha]_D^{20}$=−64.4 (c=0.87, CHCl$_3$); $^1$H NMR (300 MHz, CDCl$_3$) δ 5.15-5.04 (m, 2 H, CH=C=CH), 3.74 (s, 6 H, Me×2), 3.51 (t, J=7.5 Hz, 1 H, CFI), 2.62-2.54 (m, 2 H, CH$_2$), 1.90-1.82 (m, 2 H, CH$_2$), 1.72-1.56 (m, 1 H, CH), 0.910 (d, J=6.6 Hz, 3 H, Me), 0.906 (d, J=6.6 Hz, 3 H, Me); $^{13}$C NMR (75 MHz, CDCl$_3$) δ 204.6, 169.3, 169.2, 91.3, 86.6, 52.4, 51.3, 38.2, 28.3, 28.0, 22.09, 22.06; IR (neat) ν (cm$^{-1}$) 2956, 2927, 2869, 1964, 1754, 1739, 1436, 1342, 1271, 1232, 1154, 1044; MS (EI) m/z (%): 240 (M$^+$, 27.06), 97 (100); HRMS calcd for C$_{13}$H$_{20}$O$_4$ [M$^+$]: 240.1362; Found: 240.1362.

EXAMPLE 33

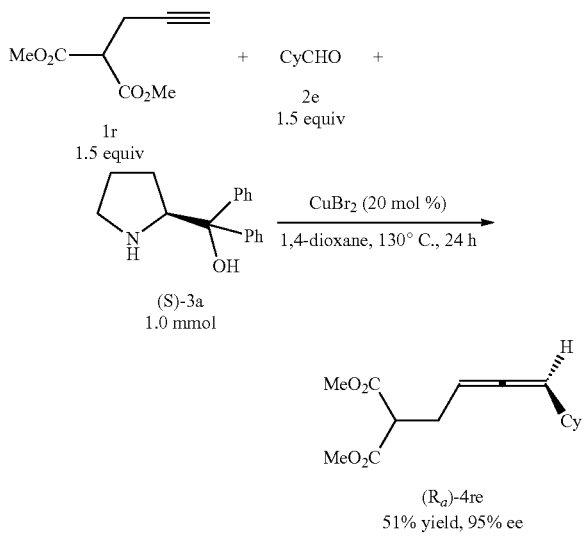

(R$_a$)-4re
51% yield, 95% ee

Following the procedure of Example 17. The reaction of CuBr$_2$ (44.8 mg, 0.2 mmol), 1r (255.7 mg, 1.5 mmol), (S)-3a (252.8 mg, 1.0 mmol), and 2e (168.2 mg, 1.5 mmol) in dioxane (3.0 mL) afforded (R$_a$)-4re (135.7 mg, 51%) (eluent: petroleum ether/ethyl acetate=15/1) as a liquid: 95% ee (HPLC conditions: Chiralcel OD-H column, hexane/i-

PrOH=100/1, 1.0 mL/min, λ=214 nm, $t_R$(minor)=9.0 min, $t_R$(major)=9.6 min); $[α]_D^{20}$=−84.0 (c=1.045, CHCl$_3$) (reported value: 99% ee; $[α]_D^{20}$=−85.4 (c=1.05, CHCl$_3$)); $^1$H NMR (300 MHz, CDCl$_3$) δ 5.20-5.08 (m, 2 H, CH=C=CH), 3.740 (s, 3 H, Me), 3.737 (s, 3 H, Me), 3.51 (t, J=7.5 Hz, 1 H, CH), 2.63-2.54 (m, 2 H, CH$_2$), 2.00-1.85 (m, 1 H, CH from Cy), 1.78-1.57 (m, 5 H, five protons from Cy), 1.35-0.95 (m, 5 H, five protons from Cy); $^{13}$C NMR (75 MHz, CDCl$_3$) δ 202.7, 169.33, 169.29, 98.9, 88.2, 52.4, 51.2, 37.1, 32.82, 32.78, 28.0, 26.0, 25.9; IR (neat) ν (cm$^{-1}$) 2926, 2851, 1959, 1757, 1738, 1617, 1436, 1343, 1233, 1155, 1035; MS (EI) m/z (%): 266 (M$^+$, 6.72), 91 (100). (reference: J. Ye, W. Fan, S. Ma, *Chem. Eur. J.* 2013, 19, 716).

EXAMPLE 34

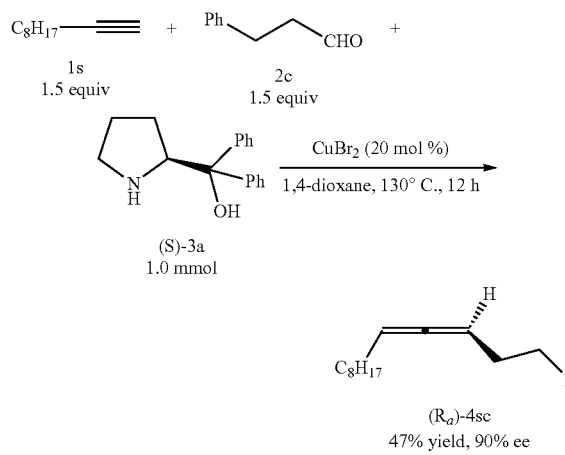

(R$_a$)-4sc
47% yield, 90% ee

Following the procedure of Example 17. The reaction of CuBr$_2$ (44.9 mg, 0.2 mmol), 1s (207.8 mg, 1.5 mmol), (S)-3a (253.4 mg, 1.0 mmol), and 2c (201.5 mg, 1.5 mmol) in dioxane (3.0 mL) afforded (R$_a$)-4sc (119.3 mg, 47%) (eluent: petroleum ether) as a liquid: 90% ee (HPLC conditions: Chiralcel OD-H column, hexane/i-PrOH=100/0, 0.3 mL/min, λ=214 nm, $t_R$(minor)=17.9 min, $t_R$(major)=19.7 min); $[α]_D^{20}$=−50.0 (c=0.84, CHCl$_3$); $^1$H NMR (300 MHz, CDCl$_3$) δ 7.30-7.21 (m, 2 H, ArH), 7.21-7.12 (m, 3 H, ArH), 5.16-5.02 (m, 2 H, CH=C=CH), 2.72 (t, J=7.8 Hz, 2 H, CH$_2$), 2.35-2.20 (m, 2 H, CH$_2$), 1.99-1.87 (m, 2H, CH$_2$), 1.42-1.18 (m, 12 H, CH$_2$×6), 0.88 (t, J=6.8 Hz, 3H, Me); $^{13}$C NMR (75 MHz, CDCl$_3$) δ 204.0, 141.9, 128.5, 128.2, 125.8, 91.5, 90.2, 35.5, 31.9, 30.7, 29.4, 29.3, 29.2, 29.1, 28.9, 22.7, 14.1; IR (neat) ν (cm$^{-1}$) 3086, 3063, 3027, 2924, 2854, 1962, 1721, 1604, 1496, 1455, 1373, 1331, 1284, 1075, 1028; MS (EI) m/z (%): 256 (M$^+$, 12.85), 91 (100); HRMS calcd for C$_{19}$H$_{28}$ [M$^+$]: 256.2191, found: 256.2194.

EXAMPLE 35

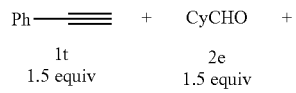

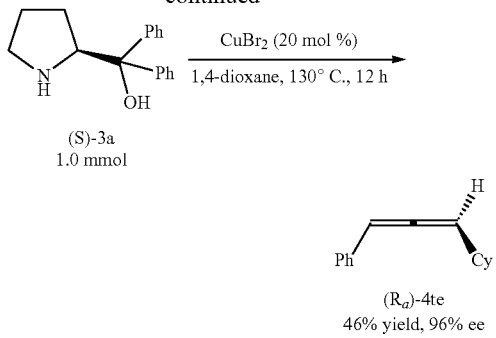

(R$_a$)-4te
46% yield, 96% ee

Following the procedure of Example 17. The reaction of CuBr$_2$ (44.8 mg, 0.2 mmol), 1t (153.2 mg, 1.5 mmol), (S)-3a (253.1 mg, 1.0 mmol), and 2e (168.4 mg, 1.5 mmol) in dioxane (3.0 mL) afforded (R$_a$)-4te (90.1 mg, 46%) (eluent: petroleum ether) as a liquid: 96% ee (HPLC conditions: Chiralcel OD-H column, hexane/i-PrOH=100/0, 0.3 mL/min, λ=214 nm, $t_R$(major)=20.1 min, $t_R$(minor)=22.1 min); $[α]_D^{20}$=−355.3 (c=1.01, CHCl$_3$) (reported value: 99% ee; $[α]_D^{19}$=−330.3 (c=0.94, CHCl$_3$)) (The results we repeated the reaction in ref. 3: 99% ee; $[α]_D^{20}$=−379.0 (c=1.125, CHCl$_3$)); $^1$H NMR (300 MHz, CDCl$_3$) δ 7.32-7.23 (m, 4 H, ArH), 7.21-7.11 (m, 1 H, ArH), 6.15 (dd, J$_1$=6.6 Hz, J$_2$=3.0 Hz, 1 H, one proton from CH=C=CH), 5.56 (t, J=6.3 Hz, 1 H, one proton from CH=C=CH), 2.20-2.04 (m, 1 H, CH), 1.90-1.57 (m, 5 H, five protons from Cy), 1.38-1.09 (m, 5 H, five protons from Cy); $^{13}$C NMR (75 MHz, CDCl$_3$) δ 204.1, 135.2, 128.5, 126.6, 126.4, 101.0, 95.4, 37.6, 33.2, 33.1, 26.1, 26.0; IR (neat) ν (cm$^{-1}$) 3082, 3062, 3030, 2924, 2851, 1946, 1597, 1496, 1458, 1257, 1071, 1028; MS (EI) m/z (%): 198 (M$^+$, 30.22), 130 (100). (reference: R. Lü, J. Ye, T. Cao, B. Chen, W. Fan, W. Lin, J. Liu, H. Luo, B. Miao, S. Ni, X. Tang, N. Wang, Y. Wang, X. Xie, Q. Yu, W. Yuan, W. Zhang, C. Zhu, S. Ma, *Org. Lett.* 2013, 15, 2254).

Finally, it should be noted that the above mentioned is just only some specific examples of the present invention. Obviously, the present invention is not limited to the above examples, which can have many variations. All the modifications derived directly or envisaged by a person skilled in the art from the disclosure of the present invention shall fall within the scope of the present invention.

What is claimed:
1. A process for synthesizing optically active 1,3-disubstituted allenes, in a heated reaction comprising a functionalized terminal alkyne, an aldehyde and a chiral secondary amine as reactants, a divalent copper salt as a catalyst and an organic solvent, thereby producing a variety of functionalized axially chiral 1,3-disubstituted allenes; wherein the process consists of:
  adding in sequence to a reaction under nitrogen atmosphere: a divalent copper salt, a chiral secondary amine, a terminal alkyne, an aldehyde and an organic solvent;
  subjecting the reaction to anhydrous and anaerobic treatment by heating for 12-24 h in an oil bath;
  returning the reaction to room temperature,
  diluting the reaction with the organic solvent,
  washing the reaction with dilute hydrochloric acid,
  separating the organic phase,
  extracting the aqueous phase with the organic solvent,
  washing with saturated brine, drying with anhydrous sodium sulfate, filtering, concentrating and subjecting reaction products to column chromatography, so as to obtain the axially chiral allene; wherein the reaction has a following reaction equation:

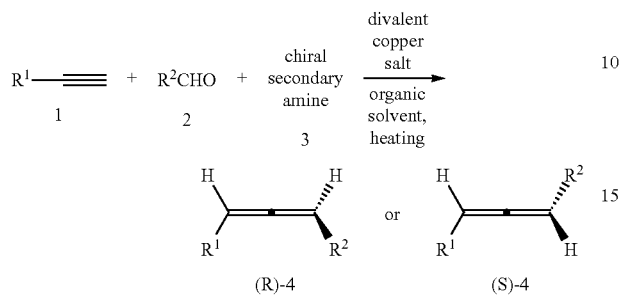

wherein $R^1$ comprises functional groups selected from glycosidic units, primary alcohols, secondary alcohols, tertiary alcohols, amides, malonates, alkyl group or aryl group, and $R^2$ is an alkyl group or an aryl group.

2. The process for synthesizing optically active 1,3-disubstituted allenes of claim 1, wherein the catalyst is copper bromide, copper chloride, copper acetate, copper sulfate or copper triflate.

3. The process for synthesizing optically active 1,3-disubstituted allenes of claim 1, wherein the chiral secondary amine is selected from the group consisting of (S)-3a and enantiomers thereof:

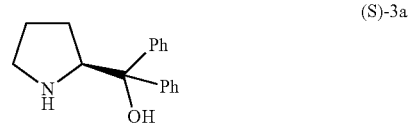 [SMILES: OC(c1ccccc1)(c1ccccc1)[C@@H]1CCCN1]

4. The process for synthesizing optically active 1,3-disubstituted allenes of claim 1, wherein the organic solvent is 1,4-dioxane, toluene, benzene, chlorobenzene, p-xylene, o-xylene, m-xylene, or mesitylene.

5. The process for synthesizing optically active 1,3-disubstituted allenes of claim 3, wherein the organic solvent is 1,4-dioxane, toluene, benzene, chlorobenzene, p-xylene, o-xylene, m-xylene, or mesitylene.

* * * * *